(12) United States Patent
Miller et al.

(10) Patent No.: US 9,604,985 B2
(45) Date of Patent: Mar. 28, 2017

(54) PROCESS FOR THE PREPARATION OF CHIRAL TERT-BUTYL 4-((1R,2S,5R)-6(BENZYLOXY)-7-OXO-1,6-DIAZABICYCLO[3.2.1]OCTANE-2-CARBOXAMIDO)PIPERIDINE-1-CARB DERIVATIVES AND (2S,5R)-7-OXO-N-PIPERIDIN-4-YL-6-(SULFOXY)-1,6-DIAZABICYCLO[3.2.1] OCTANE-2-CARBOXAMIDE

(71) Applicant: Merck Sharp & Dohme Corp., Rahway, NJ (US)

(72) Inventors: Steven P. Miller, Monroe, NJ (US); John Limanto, Jersey City, NJ (US); Yong-Li Zhong, Edison, NJ (US); Nobuyoshi Yasuda, Mountainside, NJ (US); Zhijian Liu, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/897,290

(22) PCT Filed: Jun. 5, 2014

(86) PCT No.: PCT/US2014/040983
§ 371 (c)(1),
(2) Date: Dec. 10, 2015

(87) PCT Pub. No.: WO2014/200786
PCT Pub. Date: Dec. 18, 2014

(65) Prior Publication Data
US 2016/0122350 A1   May 5, 2016

Related U.S. Application Data

(60) Provisional application No. 61/833,108, filed on Jun. 10, 2013, provisional application No. 61/886,759, filed on Oct. 4, 2013.

(51) Int. Cl.
*C07D 471/08* (2006.01)
*C07D 401/12* (2006.01)
(Continued)

(52) U.S. Cl.
CPC .......... *C07D 471/08* (2013.01); *C07D 211/62* (2013.01); *C07D 401/12* (2013.01); *C07D 491/08* (2013.01); *Y02P 20/55* (2015.11)

(58) Field of Classification Search
CPC .................. C07D 471/08; C07D 401/12
See application file for complete search history.

(56) References Cited

U.S. PATENT DOCUMENTS 5,510,343 A      4/1996   Charnas et al.
2003/0199541 A1  10/2003  Lampilas et al.
(Continued)

FOREIGN PATENT DOCUMENTS

WO   WO2008/039420   4/2008
WO   WO2009/091856   7/2009
WO   WO2010/126820   11/2010

OTHER PUBLICATIONS

Baldwin, Jack E., A Novel Entry to Carbenoid Species via Beta-Ketosulfoxonium Ylides, J. Chem. Soc., Chem. Commun., 1993, 1434-1435, 18.
(Continued)

*Primary Examiner* — Kahsay Habte
(74) *Attorney, Agent, or Firm* — Henry P. Wu; Gloria M. Fuentes

(57) ABSTRACT

A process for the preparation of N-protected 6-(piperidin-4-ylcarbamoyl)piperidin-3-yl sulfonates of Formula (III): which comprises contacting a lactone of Formula (II): with an azacycloalkylamine of formula (II-Am): followed by contact with a sulfonyl halide of formula (II-Su): $R^4$—$SO_2W$ (II-Su) in the presence of tertiary amine base, wherein $P^{G1}$ and $P^{G2}$ are amine protective groups; k, p and q are 0, 1, or 2, and W, $R^2$, $R^3$, $R^4$, $R^5$, $R^6$, $R^7$, $R^8$, and $R^9$ are defined herein. Additional embodiments add a series of process steps leading to the synthesis of 7-oxo-1,6-diazabicyclo[3.2.1]octanes suitable for use as β-lactamase inhibitors.

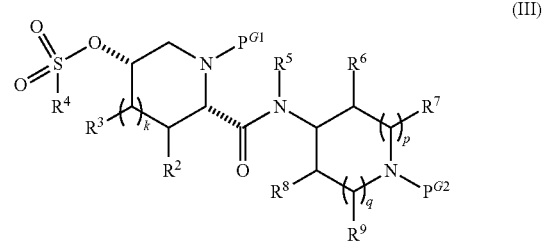

(III)

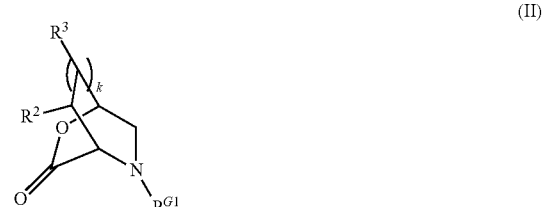

(II)

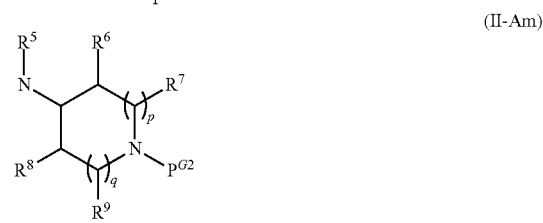

(II-Am)

24 Claims, No Drawings

(51) Int. Cl.
*C07D 491/08* (2006.01)
*C07D 211/62* (2006.01)

(56) References Cited

U.S. PATENT DOCUMENTS

2011/0294777 A1    12/2011    Blizzard et al.
2012/0053350 A1     3/2012    Mangion et al.

OTHER PUBLICATIONS

Mangion, Ian K., Iridium-Catalyzed X-H insertions of Sulfoxonium Ylides, Organic Letters, 2009, 3566-3569, 11(16).
Mangion, Ian K., A Concise Synthesis of a Beta-Lactamase Inhibitor, Organic Letters, 2011, 5480-5483, 13(20).
Mark C. Noe et al., Discovery of 3,3-dimethyl-5-hydroxypipecolic hydroxamate-based inhibitors of aggrecanase and MMP-13, Bioorganic and Medicinal Chemistry Letters, 2005, 2808-2811, 15(11).
Michael A. Letavic et al., Synthesis and Biological Activity of Selective Pipecolic Acid-Based TNF-beta Converting Enzyme (TACE) Inhibitors, Bioorganic and Medicinal Chemistry Letters, 2002, 1387-1390, 12(10).
Steven P. Miller et al., Practical and Cost-Effective Manufacturing Route for the Synthesis of a Beta-Lactamase Inhibitor, Organic Letters, 2013, 174-177, 16.

PROCESS FOR THE PREPARATION OF CHIRAL TERT-BUTYL 4-((1R,2S,5R)-6(BENZYLOXY)-7-OXO-1,6-DIAZABICYCLO[3.2.1]OCTANE-2-CARBOXAMIDO)PIPERIDINE-1-CARB DERIVATIVES AND (2S,5R)-7-OXO-N-PIPERIDIN-4-YL-6-(SULFOXY)-1,6-DIAZABICYCLO[3.2.1] OCTANE-2-CARBOXAMIDE

FIELD OF THE INVENTION

The invention is related to the preparation of N-protected 6-(piperidin-4-ylcarbamoyl)piperidin-3-yl sulfonates. These sulfonates are suitable for use as intermediates that lead via a series of additional process steps to the synthesis of 7-oxo-1,6-diazabicyclo[3.2.1]octane-2-carboxamides and esters. The invention is also related to a final process step for the preparation of, the beta lactamase inhibitor, (2S,5R)-7-oxo-N-piperidin-4-yl-6-(sulfoxy)-1,6-diazabicyclo[3.2.1]octane-2-carboxamide.

BACKGROUND OF THE INVENTION

Certain 7-oxo-1,6-diazabicyclo[3.2.1]octane-2-carboxamides are inhibitors of β-lactamase and, when used in conjunction with β-lactam antibiotics, can be effective for the treatment of bacterial infections. See, for example, International Patent Application Publication No. WO2009/091856 which discloses 7-oxo-1,6-diazabicyclo[3.2.1]octane-2-carboxamides and their synthesis from a ketosulfoxonium ylide intermediate containing an amide side chain, where the ylide intermediate is cyclized to a 5-oxo-piperidine-2-carboxamide using an Ir, Rh, or Ru catalyst. Similarly, Baldwin et al. disclose the transformation of lactone-derived β-ketosulfoxonium ylides into β-oxonitrogen heterocycles in the presence of a rhodium catalyst. See Baldwin et al., 1993, *J. Chem. Soc., Chem. Commun.* 18:1434-1435. Mangion et al. disclose iridium-catalyzed X-H insertions (e.g., N-H insertions) of sulfoxonium ylides. See Mangion et al., 2009, *Org. Lett.*, 11:3566-3569 and Mangion et al., 2011, *Org. Lett.* 13:5480-5483.

U.S. Patent Application Publication No. US2003/0199541 discloses methods for preparing azabicyclic compounds which are useful as medicaments, in particular anti-bacterial agents. International Patent Application Publication No. WO2008/039420 discloses methods for preparing certain 7-oxo-2,6-diazabicyclo[3.2.0]heptane-2-carboxamides which are useful as 3-lactamase inhibitors.

International Patent Application Publication No. WO2010/126820 discloses the preparation of alkyl esters of N-protected oxo-azacycloalkylcarboxylic acids. These esters can be used as intermediates in the synthesis of 7-oxo-1,6-diazabicyclo[3.2.1]octane-2-carboxamides and esters.

SUMMARY OF THE INVENTION

The present invention provides a process for preparing a compound of Formula III:

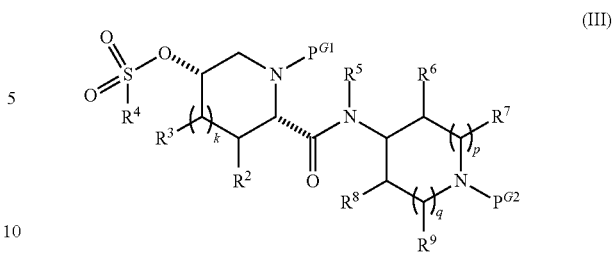

(III)

which comprises:
(B) contacting a lactone of Formula II:

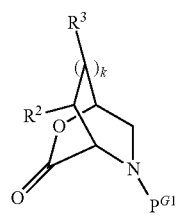

(II)

with an azacycloalkylamine of formula II-Am:

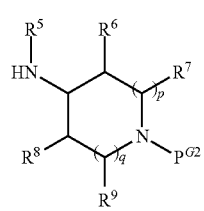

(II-Am)

followed by contact with a sulfonyl halide of formula II-Su:

$R^4$—$SO_2W$     (II-Su)

in the presence of tertiary amine base to obtain a compound of Formula III wherein:
$P^{G1}$ is a first amine protecting group which forms with the amino nitrogen to which it is attached a carbamate, a benzylamine, or a sulfonamide;
$P^{G2}$ is a second amine protecting group selected from (i) carbamates and (ii) benzylamines; k is an integer equal to 0, 1, or 2;
$R^2$ and $R^3$ are defined as follows:
  (a) $R^2$ is H, $C_{1-6}$ alkyl, —O—$C_{1-6}$ alkyl, —O—Si(—$C_{1-6}$ alkyl)$_3$, or —O—Si(—$C_{1-6}$ alkyl)(-phenyl)$_2$, and each $R^3$ is independently H or $C_{1-6}$ alkyl; or
  (b) alternatively and with the proviso that k is 1 or 2, $R^2$ and the $R^3$ adjacent to $R^2$ together with the carbon atoms to which each is attached form $C_{5-7}$ cycloalkyl which is optionally substituted with from 1 to 3 substituents each of which is independently $C_{1-6}$ alkyl, —O—$C_{1-6}$ alkyl, —O—Si(—$C_{1-6}$ alkyl)$_3$, or —O—Si(—$C_{1-6}$ alkyl)(-phenyl)$_2$; and any other $R^3$ is H or $C_{1-6}$ alkyl;
$R^4$ is:
  (1) phenyl optionally substituted with from 1 to 3 substituents each of which is independently $C_{1-4}$ alkyl, $C_{1-4}$ haloalkyl, —O—$C_{1-4}$ alkyl, —O—$C_{1-4}$ haloalkyl, Cl, Br, F, or $NO_2$;

(2) $C_{1-4}$ alkyl; or
(3) $C_{1-4}$ haloalkyl;
$R^5$ is H or $C_{1-3}$ alkyl;
$R^6$ and $R^8$ are independently H, $C_{1-3}$ alkyl, —O—$C_{1-3}$ alkyl, or —N(—$C_{1-3}$ alkyl)$_2$; each $R^7$ and $R^9$ is independently H or $C_{1-6}$ alkyl;
W is halogen;
p is 0, 1, or 2;
q is 0, 1, or 2; and
p+q=0, 1, 2, or 3.

Compound III is useful as an intermediate that in combination with a series of additional steps (described below) results in a convergent synthesis of 7-oxo-1,6-diazabicyclo[3.2.1]octane-2-carboxamides and 2-carboxylic esters that can be used as β-lactamase inhibitors (BLIs). The use of Compound III also provides for more flexibility in that it offers a more direct route to 7-oxo-1,6-diazabicyclo[3.2.1]octane-2-carboxylic esters suitable for use as BLIs. The number of overall synthetic steps is reduced and the cost and Process Mass Intensity are lowered compared to the process described in Mangion et al., 2011, *Org Lett* 13:5480-5483. A number of toxic, expensive, or difficult to handle reagents are replaced using this process versus the process in Mangion et al., 2011, *Org Lett* 13:5480-5483. Furthermore, the use of Compound III permits the introduction of amide side chains that can be chemically unstable to reaction conditions required in early synthetic steps. Additionally, an improved method of removing a Boc protecting group allows for increased yields and lower Process Mass Intensity.

Other embodiments, aspects and features of the present invention are either further described in or will be apparent from the ensuing description, examples, and appended claims.

DETAILED DESCRIPTION OF THE INVENTION

The present invention (alternatively referred to herein as "Process P") includes a process for preparing a compound of Formula III which comprises Step B as set forth above in the Summary of the Invention. Step B involves the nucleophilic opening of a lactone with an amine directly, without the use of coupling reagents. Step B avoids the use of alternate procedures, such as the generation of a diazoketone or ketosulfoxonium ylide to perform cyclizations which necessitate expensive transition metals or explosive hazards such as diazomethane. In certain embodiments, Step B can also provide a high yield; i.e., yields of 95% or higher. A compound of Formula III is useful as an intermediate in the process for the synthesis of the beta-lactamase inhibitor, (2S,5R)-7-oxo-N-piperidin-4-yl-6-(sulfoxy)-1,6-diazabicyclo[3.2.1]octane-2-carboxamide. The overall process for the synthesis of (2S,5R)-7-oxo-N-piperidin-4-yl-6-(sulfoxy)-1,6-diazabicyclo[3.2.1]octane-2-carboxamide is shortened in part because it starts with a different material.

The choice of different protecting groups allows for the displacement to run at a high yield, avoiding the multi-step protection/deprotection and formation of large amounts of byproducts. Proper and appropriate choice of protecting groups and activating agents allows selective reaction conditions to be used to minimize by-products during the displacement (Step C). These new protecting groups allow the hydrogenation to be run without tedious monitoring of reagents and by-product formation as a protecting group switch is no longer needed (Step E). Finally, a new set of conditions for the final deprotection step generates a high yield and a clean reaction, avoiding the generation of the by-products (Step G).

Overall, in certain embodiments, the present invention provides high yields (~42% overall yield), high throughput, and low cost. The process also removes several steps in the overall synthesis versus the current route (7 isolated steps in new invention versus 12 in old route). The new invention also provides improved sustainability by replacing an iridium-catalyzed reaction with an intermediate that can be obtained via biocatalysis.

The amine protective group $P^{G1}$, in step B, in combination with the amino nitrogen to which it is attached, can be a carbamate or a benzylamine or a sulfonamide. Suitable carbamate, benzylamine and sulfonamide protective groups and methods for their formation and cleavage are described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. In one embodiment, $P^{G1}$ is (1) —C(=O)—O—(CH$_2$)$_{0-1}$—CH=CH$_2$, (2) —C(=O)—O—CH$_2$-AryB, wherein AryB is phenyl which is optionally substituted with from 1 to 3 substituents each of which is independently halo, —NO$_2$, —C$_{1-4}$ alkyl, or —O—C$_{1-4}$ alkyl, (3) —C(=O)—O—C$_{1-4}$ alkyl, or (4) —CH$_2$-AryC in which AryC is phenyl which is optionally substituted with from 1 to 3 substituents each of which is independently halo, —NO$_2$, —C$_{1-4}$ alkyl, or —O—C$_{1-4}$ alkyl. In another embodiment, $P^{G1}$ is t-butyloxycarbonyl (Boc), allyloxycarbonyl (Alloc), benzyloxycarbonyl (Cbz), p-methoxybenzyloxycarbonyl, p-nitrobenzyloxycarbonyl, p-bromobenzyloxycarbonyl, p-chlorobenzyloxycarbonyl, 2,4-dichlorobenzyloxycarbonyl, or benzyl. In still another embodiment, $P^{G1}$ is Boc. In still another embodiment, pG1 is a sulfonyl group generated from sulfonyl halides such as methanesulfonyl chloride, chloromethanesulfonyl chloride, dichloromethanesulfonyl chloride, benzenesufonyl chloride, p-trifluoromethylbenzenesulfonyl chloride, p-toluenesulfonyl chloride, p-bromobenzenesulfonyl chloride, p-fluorobenzenesulfonyl chloride, p-methoxybenzenesulfonyl chloride, 2-nitrobenzenesulfonyl chloride, 4-nitrobenzenesulfonyl chloride, and 2,4-dichlorobenzenesulfonyl chloride, chloromethanesulfonyl chloride, p-trifluoromethylbenzenesulfonyl chloride, p-bromobenzenesulfonyl chloride, and 2,4-dichlorobenzenesulfonyl chloride, chloromethanesulfonyl chloride, p-trifluoromethylbenzenesulfonyl chloride and p-bromobenzenesulfonyl chloride. A preferred sulfonyl halide is 2-nitrobenzenesulfonyl chloride.

$P^{G2}$ is an amine protective group which is not labile under conditions which the $P^{G1}$ group is labile. In other words, $P^{G2}$ is a group which is not cleaved under conditions suitable for the removal of $P^{G1}$. $P^{G2}$, in combination with the amino nitrogen to which it is attached, is suitably an alkyl carbamate, aryl carbamate, vinyl carbamate, allyl carbamate, an acetamide (including trifluoroacetamide) or a benzylamine. Suitable $P^{G2}$ groups include Boc, Cbz, Alloc, p-methoxybenzyl, and benzyl. A preferred $P^{G2}$ is Boc.

Amines of Formula II-Am can be prepared, for example, by reductive amination of the corresponding ketone or by hydride reduction of the corresponding imine. Further description of methods suitable for the preparation of amines of Formula II-Am can be found in Richard Larock, *Comprehensive Organic Transformations*, 2$^{nd}$ edition, Wiley-VCH Publishers Inc, 1999, pp 753-879.

Step B is conducted in an organic solvent. Suitable solvents include DCE, THF, DMF, NMP, DMSO, 1,4- dioxane, dimethylacetamide, toluene, xylenes, chlorobenzene, trifluorotoluene, 2-methyl-THF and acetonitrile. Preferred solvents are THF and acetonitrile.

The addition of amine of Formula II-Am in step B can be conducted at a temperature from about 25° C. to about 100° C. for 2 to 72 hours or 10 to 72 hours and is typically conducted at a temperature in a range from about 60° C. to about 85° C. for 8 to 24 hours or 15 to 24 hours. As used herein, the term "about" can refer to a deviation of ±5%, ±10%, or ±15%.

The addition of sulfonyl halide of Formula II-Su in Step B can suitably conducted in the presence of a tertiary amine base over the course of 10 minutes to 10 hours, preferably 30 minutes to 90 minutes.

A class of suitable tertiary amines includes TEA, DIPEA, 4-NMM and 4-dimethylaminopyridine. 4-Dimethylaminopyridine is a preferred base. The base is typically employed in the amount in a range of from about 1 to about 3 equivalents per equivalent of Compound III, and is more typically employed in an amount in a range of from about 1.1 to about 2 equivalents (e.g., about 1.6 equivalents).

Exemplary sulfonyl halides suitable for use in Step B include methanesulfonyl chloride, chloromethanesulfonyl chloride, dichloromethanesulfonyl chloride, benzenesufonyl chloride, p-trifluoromethylbenzenesulfonyl chloride, p-toluenesulfonyl chloride, p-bromobenzenesulfonyl chloride, p-fluorobenzenesulfonyl chloride, p-methoxybenzenesulfonyl chloride, 2-nitrobenzenesulfonyl chloride, 4-nitrobenzenesulfonyl chloride, and 2,4-dichlorobenzenesulfonyl chloride. A class of suitable sulfonyl halides consists of chloromethanesulfonyl chloride, p-trifluoromethylbenzenesulfonyl chloride, p-bromobenzenesulfonyl chloride, and 2,4-dichlorobenzenesulfonyl chloride. Another class of suitable sulfonyl halides consists of chloromethanesulfonyl chloride, p-trifluoromethylbenzenesulfonyl chloride, 2-nitrobenzenesulfonyl chloride and p-bromobenzenesulfonyl chloride. A preferred sulfonyl halide is p-trifluoromethylbenzenesulfonyl chloride. Another preferred sulfonyl halide is 2-nitrobenzenesulfonyl chloride. The sulfonyl halide is typically employed in an amount in a range of from about 1 to about 2 equivalents per equivalent of Compound III, and is more typically employed in an amount in a range of from about 1 to about 1.5 equivalents (e.g., about 1.3 equivalents).

The addition of sulfonyl halide of Formula II-Su in Step B can be conducted at a temperature from about 0° C. to about 50° C. and is typically conducted at a temperature in a range from about 10° C. to about 30° C. over the course of 30 minutes to 90 minutes.

Other embodiments of Compound III and Step B include the following:
(1a) k is 0 or 1;
(1b) k is 0;
(1c) k is 1;
(2a) $R^2$ is H, $C_{1-4}$ alkyl, —O—$C_{1-4}$ alkyl, —O—Si(—$C_{1-4}$ alkyl)$_3$, or —O—Si(—$C_{1-4}$ alkyl)(phenyl)$_2$, and each $R^3$ is H or $C_{1-4}$ alkyl;
(2b) $R^2$ is H, $CH_3$, —$OCH_3$, —O-trimethylsilyl (TMS), —O-t-butyldiphenylsilyl (TBDPS), —O-t-butyldimethylsilyl (TBS), or —O-triisopropylsilyl (TIPS), and each $R^3$ is H or $CH_3$;
(2c) $R^2$ is H or $CH_3$, and each $R^3$ is H or $CH_3$;
(2d) $R^2$ is H, and each $R^3$ is H;
(2e) with the proviso that k is 1 or 2, $R^2$ and the $R^3$ adjacent to $R^2$ together with the carbon atoms to which each is attached form $C_{5-6}$ cycloalkyl; and any other $R^3$ is H.

One or more of these embodiments (1) to (2) can be combined with each other, wherein each such combination is a separate embodiment of Compound III and Step B. In other words, any embodiment from group 1 (1a, 1b, or 1c) can be combined with any embodiment from group 2 (2a, 2b, 2c, 2d or 2e).

An embodiment of Process P comprises Step B as just described above and further comprises:
(A) Contacting a compound of Formula I:

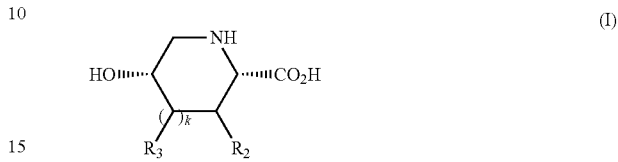

with a $P^{G1}$-producing agent in the presence of an aqueous base followed by addition of a tertiary base to obtain Compound II. In one embodiment, the contacting occurs in the presence of an organic or inorganic base to obtain Compound II.

Step A is conducted in an organic solvent and water. Suitable solvents include acetone, toluene, dichloromethane, DCE, DMF, DMAC, DMSO, THF, chlorobenzene, 1,2-dichlorobenzene, cyclopentylmethyl ether, acetonitrile, EtOAc, IPAc, MeOAc, nitromethane, trifluoromethylbenzene, methyl ethyl ketone, DME, and 2-MeTHF. Preferred solvents are acetone and ethyl acetate.

The reaction in Step A can suitably be conducted at a temperature in a range of from about 0° C. to about 30° C. over the course of 10 minutes to 10 hours and is typically conducted at a temperature in a range of from about 10° C. to about 25° C. over the course of 30 minutes to 60 minutes.

Suitable $P^{G1}$-producing agents include 2-nitrobenzene-1-sulfonyl chloride, 4-nitrobenzene-1-sulfonyl chloride, and (Boc)$_2$O. The $P^{G1}$-producing agent is typically employed in an amount in a range from about 1 equivalent to about 5 equivalents and is more typically employed in an amount in a range from about 1.3 to about 2 equivalents.

Suitable organic or inorganic bases include LiOH, NaOH, KOH, Cs(OH)$_2$, Li$_2$CO$_3$, Na$_2$CO$_3$, K$_2$CO$_3$, CsCO$_3$, LiHCO$_3$, NaHCO$_3$, KHCO$_3$, Li$_3$PO$_4$, Na$_3$PO$_4$, K$_3$PO$_4$, Li$_2$HPO$_4$, NaHPO$_4$, KHPO$_4$, diisopropylamine, triethylamine, diisopropylethylamine, morpholine, 4-methylmorpholine, DABCO, DBU, pyridine, lutidine, collidine, and the like.

Suitable aqueous bases include NaOH, KOH, LiOH, K$_2$CO$_3$, Cs$_2$CO$_3$, Na$_2$CO$_3$, K$_3$PO$_4$, and Na$_3$PO$_4$. The aqueous base is typically employed in an amount in a range from about 1 equivalents to about 10 equivalents and is more typically employed in an amount in a range from about 1.5 to about 2.0 equivalents.

Suitable tertiary bases include TEA, DIPEA, 4-NMM and diethylisopropylamine. The tertiary base is typically employed in an amount in a range from about 2.0 equivalents to about 10.0 equivalents and is more typically employed in an amount in a range from about 3.0 to about 5.0 equivalents.

The tertiary amine base in Step A is typically a tri-$C_{1-4}$ alkylamine. A class of suitable tertiary amines includes TEA, DIPEA, 4-NMM and diethylisopropylamine. TEA is a preferred base. The base is typically employed in an amount in a range of from about 1 to about 3 equivalents per equivalent of Compound I, and is more typically employed in an amount in a range of from about 1.1 to about 2 equivalents (e.g., about 1.8 equivalents).

An embodiment of Process P comprises Step B as just described above or Steps A and B as just described, and further comprises:

(C) treating compound of formula III with N-4-nitrobenzenesulfonyl-O-benzylhydroxylamine in the presence of a base, followed by treatment with an nucleophilic reagent such as a thiol to obtain compound of Formula IV, or a pharmaceutically acceptable salt thereof:

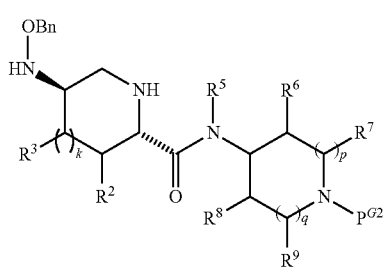

Step C is conducted in an organic solvent. Suitable solvents include DMAC, DMF, NMP, THF, methanol and DME. A preferred solvent is DMAC and methanol.

Suitable bases in Step C include Li t-butoxide, Na t-butoxide, K t-butoxide, cesium carbonate, sodium carbonate, KHMDS, and NaHMDS. A class of suitable bases consists of Li t-butoxide, Na t-butoxide, K t-butoxide, sodium carbonate and cesium carbonate. Preferred bases are K t-butoxide and sodium carbonate. The base is typically employed in an amount in a range of from about 1 to about 2 equivalents per equivalent of compound of formula III, and is more typically employed in an amount in a range of from about 1 to about 1.5 equivalents (e.g., about 1.2 equivalents).

The N-4-nitrobenzenesulfonyl-O-benzylhydroxylamine is typically employed in a range of from about 1 to about 2 equivalents per equivalent of Compound III, and is more typically employed in an amount in a range of from about 1 to about 1.5 equivalents (e.g., about 1.2 equivalents).

The reaction in Step C can suitably be conducted at a temperature in a range of from about 30° C. to about 90° C. and is typically conducted at a temperature in a range of from about 45° C. to about 70° C. over the course of 18 to 30 hours.

Suitable thiols for Step C include thiophenol or 2-mercaptoacetic acid. A preferred nucleophile is 2-mercaptoacetic acid. The acid is typically employed in an amount in a range of from about 1 to about 10 equivalents per equivalent of Compound III, and is more typically employed in an amount in a range from about 3 to about 6 equivalents.

Other embodiments of Step C include the following features of IV:
(3a) $R^5$ is H or $CH_3$;
(3b) $R^5$ is H;
(4a) $R^6$ is H or $C_{1-3}$ alkyl;
(4b) $R^6$ is H or $CH_3$;
(4c) $R^6$ is H;
(5a) p is 1 and q is 1;
(5b) p is 1 and q is 0.

One or more of these embodiments (3) to (5) can be combined with each other and/or with the embodiments described above, wherein each such combination is a separate embodiment of the compound employed in Step C.

Another embodiment of Process P comprises Steps B to C as described above or Steps A to C as described above, and further comprises:

(D) contacting Compound (IV) with phosgene, diphosgene, triphosgene, or a phosgene equivalent, such as carbodimidazole, or haloformate in the presence of a tertiary amine, and then adding an aqueous solution of acid to obtain a compound of Formula V:

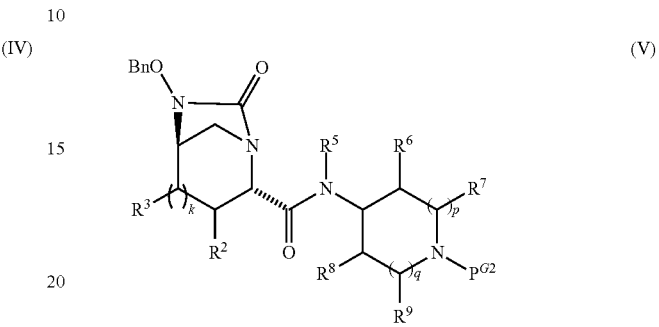

In one aspect of this embodiment, the contacting can be done in the presence of an amine base and aqueous treatment is performed to obtain a compound of formula V.

Step D is conducted in an organic solvent. Suitable solvents include DCM and acetonitrile. A preferred solvent is DCM and acetonitrile.

Suitable acids in Step D include hydrochloric acid, sulfuric acid, trifluoroacetic acid, and phosphoric acid. A preferred acid is phosphoric acid. The acid is typically employed in an amount in a range of from about 1 to about 6 equivalents per equivalent of Compound IV, and is more typically employed in an amount in a range of from about 3 to about 5 equivalents (e.g., about 3.2 equivalents).

The tertiary amine in Step D is suitably a tri-$C_{1-4}$ alkylamine. A class of suitable amines consists of TEA, DIPEA, and diethylisopropylamine. DIPEA is a preferred amine. The amine is typically employed in an amount in a range of from about 1 to about 6 equivalents per equivalent of Compound IV, and is more typically employed in an amount in a range of from about 3 to about 5 equivalents (e.g., about 3.2 equivalents).

The triphosgene, diphosgene, or phosgene or phosgene equivalent such as carbodimidazole, or haloformate is typically employed in Step D in an amount in a range of from about 0.5 to 1 equivalents per equivalent of Compound IV, and is more typically employed in an amount in a range of from about 0.7 to about 1 equivalent (e.g., about 0.8 equivalent). Triphosgene is preferred over diphosgene and phosgene.

The contacting of Compound IV with triphosgene, diphosgene, or phosgene or a phosgene equivalent such as carbodimidazole, or haloformate in Step D can suitably be conducted at a temperature in a range of from about −15° C. to about 100° C. or −15° C. to about 40° C. and is typically conducted at a temperature in a range of from about −5° C. to about 80° C. or −5° C. to about 25° C. The subsequent addition and reaction with the acid or, alternatively with aqueous treatment, can suitably be conducted at a temperature in a range of from about 0° C. to about 40 or 0° C. to about 25° C. over the course of 5 to 72 hours, typically, 10 to 30 hours.

The compound of Formula V can subsequently be processed as described in International Patent Application No. WO2010/126820 to obtain a beta lactamase inhibitor.

Thus, in another embodiment of Process P comprises Steps B to D as described above or Steps A to D as described above, and further comprises:

(E) contacting Compound V with a source of hydrogen in the presence of a hydrogenolysis catalyst to obtain a compound of Formula VI:

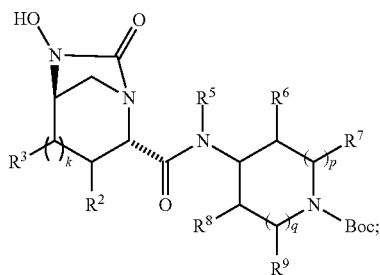

(F) contacting compound VI with a sulfating agent in the presence of an organic base to obtain a compound of Formula VII, or a pharmaceutically acceptable salt thereof:

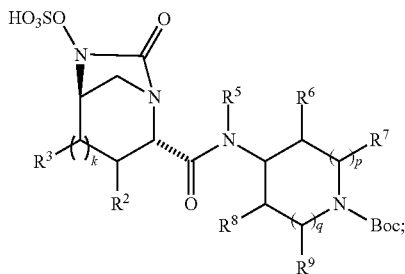

(G) treating compound VII with acid to obtain a compound of Formula VIII:

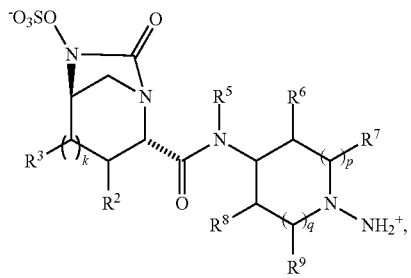

or a pharmaceutically acceptable salt thereof.

Step E is conducted in an organic solvent. Suitable solvents include ethyl acetate, DMAC, NMP, DMF, t-butanol, triethylamine, and THF. A preferred solvent is THF.

The source of hydrogen in Step E is typically hydrogen gas, optionally in a mixture with a carrier gas that is chemically inert under the reaction conditions employed in Step E (e.g., nitrogen or a noble gas such as helium or argon). The pressure is not a critical aspect in Step E, although atmospheric and superatmospheric pressures tend to be expedient. The hydrogen source can alternatively be a hydrogen-transfer molecule such as ammonium formate, cyclohexene, or cyclohexadiene.

The uptake of hydrogen is not a critical process parameter, although at least a stoichiometric amount of hydrogen gas or other hydrogen source is typically employed.

The hydrogenolysis catalyst comprises a supported or unsupported transition metals or a supported or unsupported compound, salt or complex of a transition metal. The catalyst typically employed in Step E is supported or unsupported Pd and Pt metal or a supported or unsupported Pd and Pt compound, salt or complex. Suitable catalyst supports include carbon, silica, alumina, silicon carbide, aluminum fluoride, and calcium fluoride. A class of suitable catalysts consists of Pd black (i.e., fine metallic palladium particles), $Pd(OH)_2$, Pd/C (i.e., palladium on a carbon support), $PtO_2$, and Pt/C. Pd/C is a preferred hydrogenolysis catalyst. The catalyst is typically employed in an amount in a range of from about 5 to about 20 wt. % relative to the amount of Compound V, and is more typically employed in an amount in a range of from about 5 to about 15 wt. % (e.g., about 10 wt. %).

The reaction in Step E can suitably be conducted at a temperature in a range of from about 10° C. to about 50° C. and is typically conducted at a temperature in a range of from about 15° C. to about 30° C.

The sulfating agent in Step F is suitably a complex of sulfur trioxide and an amine, wherein the amine is suitably a tertiary amine including, for example, acyclic amines (e.g., trimethylamine, TEA, DIPEA, dimethylphenylamine and dimethylbenzylamine), cyclic amines (e.g., 1-methylpyrrolidine and 1-methylpiperidine) and aromatic amines having one or more N atoms as part of the aromatic ring (e.g., 1-methylimidazole, pyridine, and pyrimidine). Halosulfonic acids (e.g., chlorosulfonic acid) and tertiary amide complexes of $SO_3$ (e.g., $DMF-SO_3$) are also suitable sulfating agents. A class of suitable sulfating agents consists of complexes of each of the following amines with sulfur trioxide: pyridine, trimethylamine, and triethylamine. Another class of suitable sulfating agents consists of pyridine-$SO_3$ complex, $DMF-SO_3$ complex and chlorosulfonic acid. The sulfating reagent is typically employed in an amount in a range of from about 1.5 to about 7.0 equivalents per equivalent of Compound VI, and is more typically employed in an amount in a range of from about 3.0 to about 4.5 equivalents.

The organic base is suitably pyridine or a tertiary amine such as 2-picoline, 2,6-lutidine, an individual trimethylpyridine, or a mixture of two or more trimethylpyridines. A class of suitable bases consists of picoline (e.g., 2-picoline), 2,6-lutidine and 2,4,6-trimethylpyridine. In a preferred embodiment, the base is 2-picoline or pyridine. The base is typically employed in an amount in a range of from about 1 to about 3 equivalents per equivalent of Compound VI, and is more typically employed in an amount in a range of from about 1.7 to about 2.2 equivalents.

Step F is conducted in an organic solvent. Suitable solvents include dichloromethane, acetonitrile, THF, DMF or pyridine. A preferred solvent is THF.

The reaction in Step F can suitably be conducted at a temperature in a range of from about 0° C. to about 40° C. and is typically conducted at a temperature in a range of from about 10° C. to about 28° C.

The acid treatment in Step G removes the Boc protecting group. The acid is suitably a mineral acid, a Lewis acid, or an organic acid. Suitable mineral acids include hydrogen halides (HCl, HBr, and HF, as a gas or in aqueous solution), sulfuric acid, tetrafluoroboric acid and nitric acid. Suitable organic acids include carboxylic acids, alkylsulfonic acids and arylsulfonic acids. Exemplary organic acids include trifluoroacetic acid (TFA), toluenesulfonic acid, benzenesulfonic acid, methanesulfonic acid, and trifluoromethanesulfonic acid. Suitable Lewis acids include $BF_3.Et_2O$, $SnCl_4$, $ZnBr_2$, $Me_3SiI$, $Me_3SiCl$, $Me_3SiBr$, $Me_3SiOTf$, and $AlCl_3$. A class of suitable acids consists of $Me_3SiOTf$, TFA, and tetrafluoroboric acid. The acid is typically employed in an amount in a range of from about 1.0 to about 2.0 equivalents per equivalent of Compound V, and is more typically employed in an amount in a range of from about 1.2 to about 1.5 equivalents. The treatment is suitably conducted at a temperature in a range of from about −10° C. to about 25° C. and is typically conducted at a temperature in a range of from about 0° C. to about 10° C. A preferred acid for the removal of the Boc protecting group in step G is trimethylsilyl iodide (TMSI), optionally in the presence of a silylating reagent such as N,O-Bis(trimethylsilyl)acetamide (BSA) or N,O-Bis(trimethylsilyl)trifluoroacetamide (TFBSA). The reaction can achieve full conversion with TMSI ranging from 0.2 equivalents to 1.5 equivalents or 0.9 equivalents to 1.5 equivalents. A preferred amount of TMSI is 0.2-1.4 equivalents or 1.2-1.4 equivalents which is added to the reaction for at least 1 hour. Preferred solvents for this reaction include MeCN and DCM at about 6 volumes to 12 volumes. The treatment is suitably conducted at a temperature in a range from −20° C. to room temperature and is typically conducted at a temperature in a range from −10 to 25° C. or 0-5° C. to initially form a TMS carbamate intermediate.

Intermediate was quenched by addition of water and a variety of alcohols (for example, primary alcohols such as MeOH, EtOH, n-PrOH, secondary alcohols such as iPA, and tertiary alcohols such as tert-BuOH). $H_2O$ is a preferred reagent to quench the reaction to provide monohydrate directly as crystalline solid. pH of the reaction mixture is optionally adjusted to neutral by addition of organic base or acid which is soluble in organic solvent, such as triethylamine, Hünig base, diisoproplyamine and diethylisopropylamine, tetra-n-butylammonium acetate, tetra-n-butylammonium hydroxide, acetic acid, propionic acid, formic acid prior to isolation of monohydrate product. The amount of $H_2O$ used for quenching has minimum impact for the reaction profile, however, high mother liquor losses were observed when high amounts of $H_2O$ were used. The optimum amount of $H_2O$ is 3-6 equivalents.

When TMSI is used, the crude product as a monohydrate can be directly isolated by filtration after the reaction, followed with a aqueous MeCN wash to afford an off-white solid. Crude product can be recrystallized from $MeCN/H_2O/$ 1-butanol system, if necessary.

Compounds encompassed by Formula VIII can exhibit inhibition of β-lactamase and thus can be used as β-lactamase inhibitors in combination with β-lactam antibiotics (e.g., imipenem, ceftazidime and piperacillin) to treat bacterial infections caused by microorganisms normally resistant to β-lactam antibiotics due to the presence of the β-lactamases. Of particular interest are compounds of Formula VIII in which $R^2=R^3=H$ and $k=1$.

A sub-embodiment of Process P is a process for preparing Compound 3:

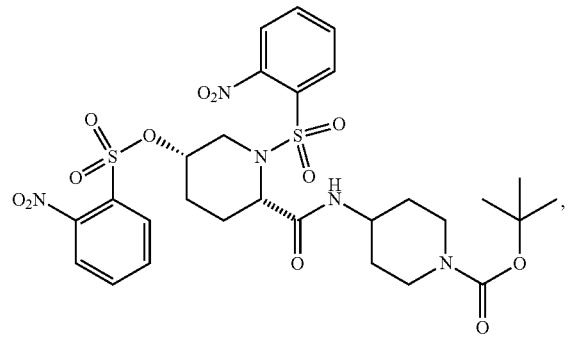

(3)

which comprises:
(B) contacting a lactone 2:

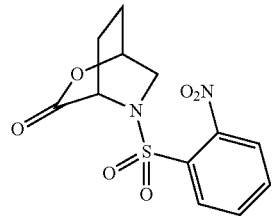

(2)

with an azacycloalkylamine 2-Am:

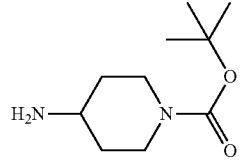

(2-Am)

followed by contact with a sulfonyl halide 2-Su:

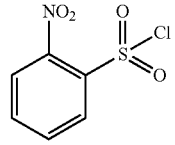

(2-Su)

in the presence of 4-dimethylaminopyridine.
Another sub-embodiment of Process P comprises Step B as just described above and further comprises:
(A) contacting a compound 1:

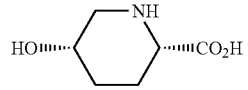

(1)

with 2-nitrobenzene-1-sulfonyl chloride in the presence of an aqueous base followed by addition of TEA, DIPEA or diethylisopropylamine to obtain compound 2. In one embodiment, contacting occurs in the presence of an organic or inorganic base to obtain compound 2.

An embodiment of Process P comprises Step B as just described above or Steps A and B as just described, and further comprises:

(C) treating Compound 3 with N-4-nitrobenzenesulfonyl-O-benzylhydroxylamine in the presence of a base, followed by treatment with an nucleophilic reagent such as a thiol to obtain compound 4, or a pharmaceutically acceptable salt thereof:

(4)

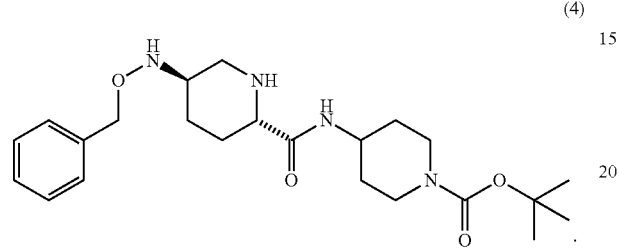

Another embodiment of Process P comprises Steps B to C as described above or Steps A to C as described above, and further comprises:

(D) contacting compound 4 with phosgene, diphosgene or triphosgene, or a phosgene equivalent such as such as carbodimidazole, or haloformate in the presence of a tri-$C_{1-4}$ alkylamine, and then adding an aqueous solution of acid to obtain a compound 5:

(5)

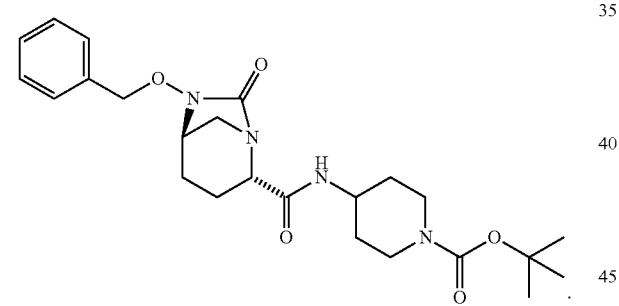

Another embodiment of Process P comprises Steps B to D as described above or Steps A to D as described above, and further comprises:

(E) contacting compound 5 with hydrogen in the presence of a Pd catalyst and optionally a Boc-producing agent selected from the group consisting of di-t-butylcarbonate and Boc-ON to obtain compound 6:

(6)

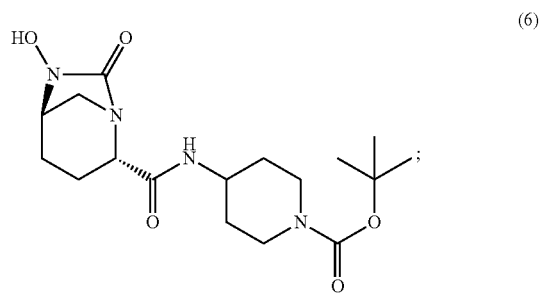 [SMILES: CC(C)(C)OC(=O)N1CCC(NC(=O)[C@@H]2CC[C@@H]3CN2C(=O)N3O)CC1]

(F) contacting compound 6 with a sulfating agent selected from the group consisting of pyridine-$SO_3$ complex, chlorosulfonic acid and DMF-$SO_3$ complex in the presence of 2-picoline to obtain compound 7, or a pharmaceutically acceptable salt thereof:

(7)

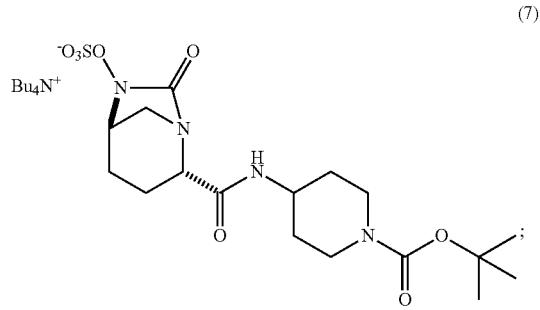

and (G) treating Compound 7 with acid to obtain Compound 8:

(8)

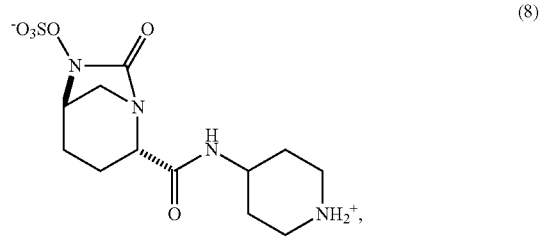

or a pharmaceutically acceptable salt thereof. In an alternative embodiment, step (F) is performed in the presence of pyridine instead of 2-picoline.

Exemplary Scheme

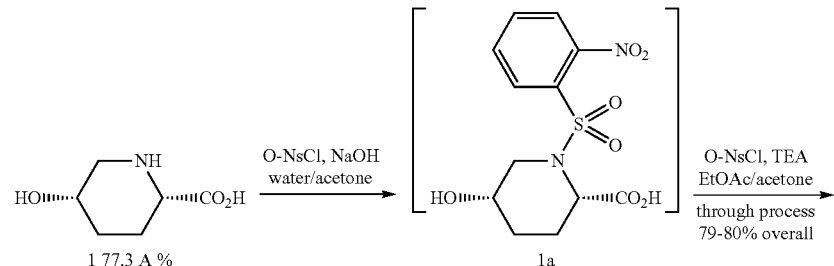

-continued
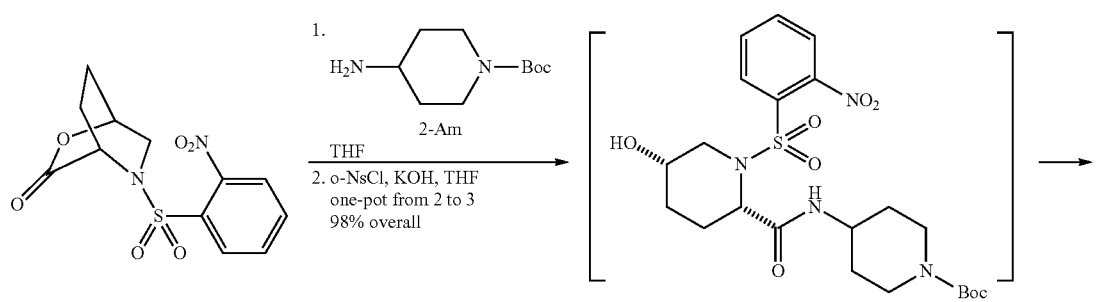
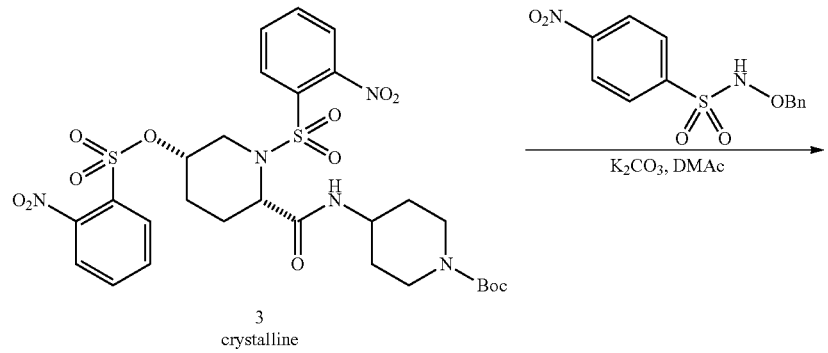
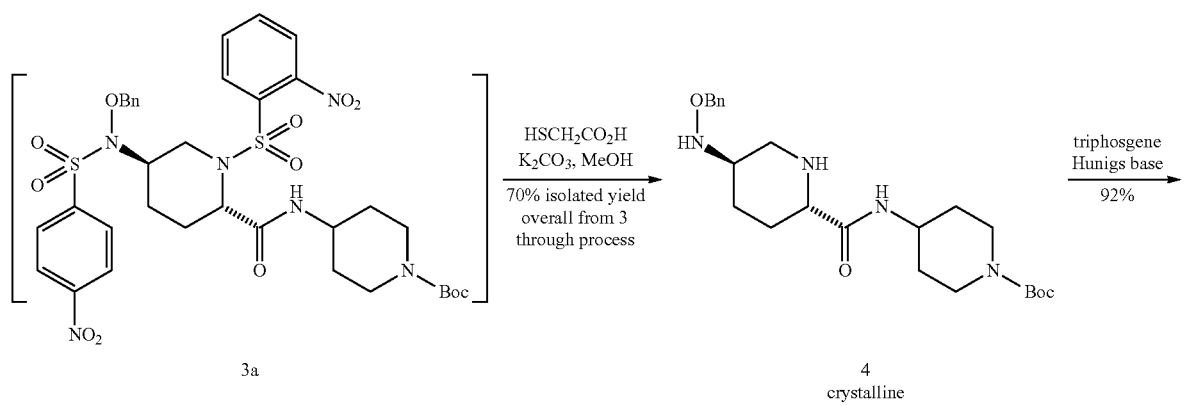
−50% isolated yield overall from 1 to 5
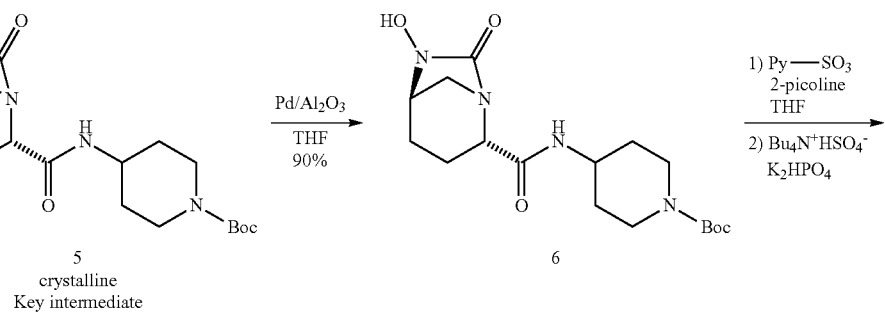

-continued

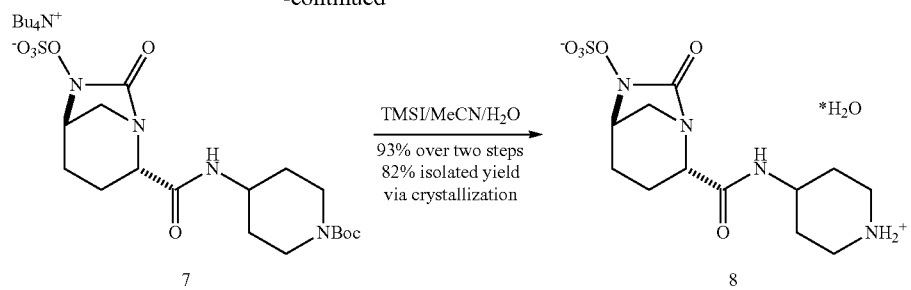

The solvents, agents, catalysts, reaction amounts, reaction temperatures, etc. described above for Steps A to G in Process P leading to Compound VIII are applicable to Steps A to G set forth in the preceding sub-embodiments leading to Compound 8, except where express limitations are placed upon one or more of these variables in the sub-embodiments.

It is to be understood that the solvents, agents, catalysts, reaction amounts, reaction temperatures, etc. described above with respect to Process P and its embodiments and sub-embodiments are intended only to illustrate, not limit, the scope of the process. For example, the solvent employed in any of Steps A to G can be any organic substance which under the reaction conditions employed in the step of interest is in the liquid phase, is chemically inert, and will dissolve, suspend, and/or disperse the reactants and any reagents so as to bring the reactants and reagents into contact and to permit the reaction to proceed. Similar considerations apply to the choice of bases, catalysts, and other reagents employed in the process steps. Furthermore, each of the steps can be conducted at any temperature at which the reaction forming the desired product can detectably proceed. The reactants, catalysts and reagents in a given step can be employed in any amounts which result in the formation of at least some of the desired product. Of course, a high conversion (e.g., at least about 60% and preferably higher) of starting materials in combination with a high yield (e.g., at least about 50% and preferably higher) of desired products is typically the objective in each step, and the choice of solvents, agents, catalysts, reaction amounts, temperatures, etc. that can provide relatively good conversions and yields of product are preferred, and the choices that can provide optimal conversions and yields are more preferred. The particular solvents, agents, catalysts, reaction amounts, reaction temperatures, etc. described above with respect to Process P and its embodiments and sub-embodiments can provide good to optimum conversions and yields.

The reaction times for the process steps described above depend upon such factors as (i) the choice and relative proportions of the starting substrate and other reagents, (ii) the choice of solvent, (iii) the choice of reaction temperature, and (iv) the level of conversion desired. The reactions are typically conducted for a time sufficient to achieve 100% or near 100% conversion (e.g., 99.5%, 99.0%, 98.0%, 97.0% or 95%).

The progress of any reaction step set forth herein can be followed by monitoring the disappearance of a reactant and/or the appearance of the desired product using such analytical techniques as TLC, HPLC, IR, NMR or GC.

Unless expressly stated to the contrary, all ranges cited herein are inclusive; i.e., the range includes the values for the upper and lower limits of the range as well as all values in between. For example, a phenyl ring described as optionally substituted with "1 to 3 substituents" is intended to include as aspects thereof, a ring substituted with 1 to 3 substituents, 2 to 3 substituents, 3 substituents, 1 to 2 substituents, 2 substituents, and 1 substituent. As another example, temperature ranges, ranges of equivalents, and the like described herein include the upper and lower limits of the range and any value in the continuum there between.

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl.

The term "branched alkyl" refers to an alkyl group as defined above except that straight chain alkyl groups in the specified range are excluded. As defined herein, branched alkyl includes alkyl groups in which the alkyl is attached to the rest of the compound via a secondary or tertiary carbon; e.g., isopropyl is a branched alkyl group.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-4}$ haloalkyl" (or "$C_1$-$C_4$ haloalkyl") refers to a $C_1$ to $C_4$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.)

The present invention also relates to a compound of:

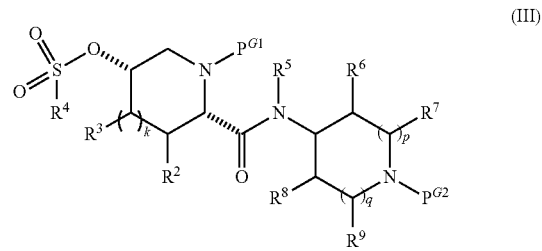

(III)

wherein:

$P^{G1}$ is a first amine protecting group which forms with the amino nitrogen to which it is attached a carbamate, a benzylamine, or a sulfonamide;

P$^{G2}$ is a second amine protecting group selected from (i) carbamates and (ii) benzylamines.

k is an integer equal to 0, 1, or 2;

R$^2$ and R$^3$ are defined as follows:
- (a) R$^2$ is H, C$_{1-6}$ alkyl, —O—C$_{1-6}$ alkyl, —O—Si(—C$_{1-6}$ alkyl)$_3$, or —O—Si(—C$_{1-6}$ alkyl)(-phenyl)$_2$, and each R$^3$ is H or C$_{1-6}$ alkyl; or
- (b) alternatively and with the proviso that k is 1 or 2, R$^2$ and the R$^3$ adjacent to R$^2$ together with the carbon atoms to which each is attached form C$_{5-7}$ cycloalkyl which is optionally substituted with from 1 to 3 substituents each of which is independently C$_{1-6}$ alkyl, —O—C$_{1-6}$ alkyl, —O—Si(—C$_{1-6}$ alkyl)$_3$, or —O—Si(—C$_{1-6}$ alkyl)(-phenyl)$_2$; and any other R$^3$ is H or C$_{1-6}$ alkyl;

R$^4$ is:
- (1) phenyl optionally substituted with from 1 to 3 substituents each of which is independently C$_{1-4}$ alkyl, C$_{1-4}$ haloalkyl, —O—C$_{1-4}$ alkyl, —O—C$_{1-4}$ haloalkyl, Cl, Br, F, or NO$_2$;
- (2) C$_{1-4}$ alkyl; or
- (3) C$_{1-4}$ haloalkyl;

R$^5$ is H or C$_{1-3}$ alkyl;

R$^6$ and R$^8$ are independently H, C$_{1-3}$ alkyl, —O—C$_{1-3}$ alkyl, or —N(—C$_{1-3}$ alkyl)$_2$;

each R$^7$ and R$^9$ is independently H or C$_{1-6}$ alkyl;

W is halogen;

p is 0, 1, or 2;

q is 0, 1, or 2; and p+q=0, 1, 2, or 3.

The present invention further relates to compounds including:

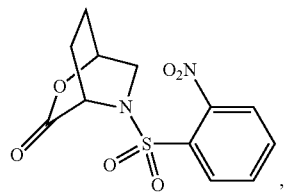
,

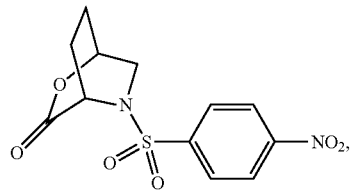
,

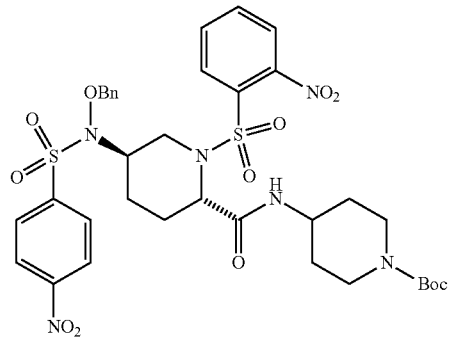

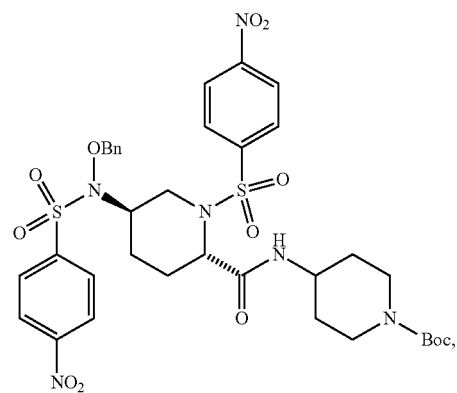

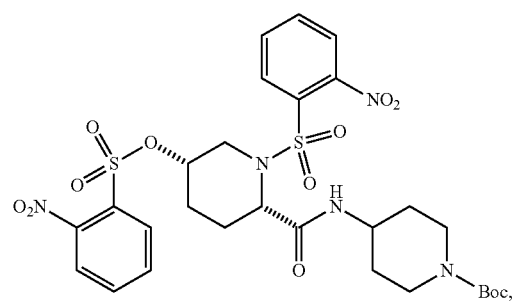

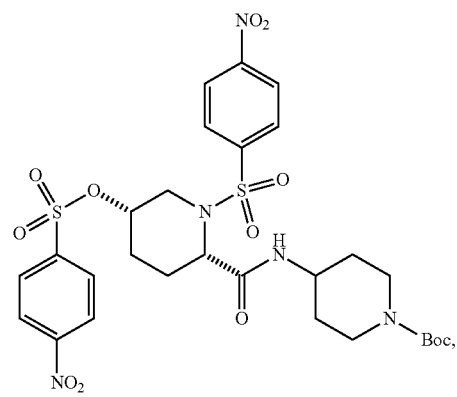

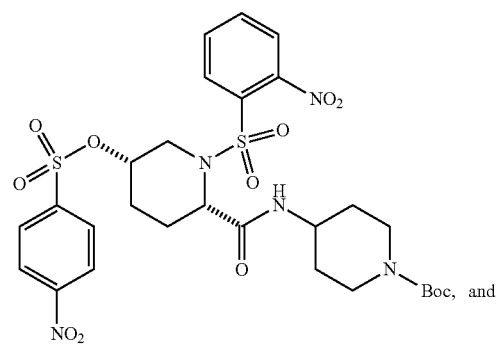

-continued

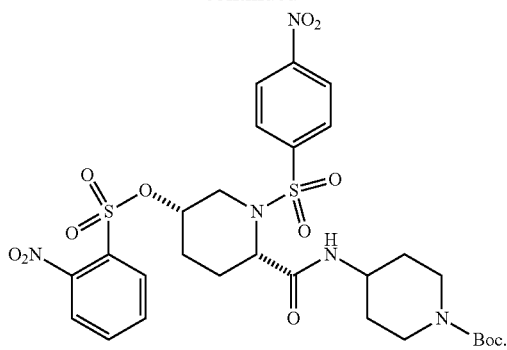

Abbreviations employed herein include the following:

| | |
|---|---|
| Alloc | allyloxycarbonyl |
| BLI | beta-lactamase inhibitor |
| Bn | benzyl |
| Boc | t-butyloxycarbonyl |
| Boc-ON | 2-(tert-butoxycarbonyloxyamino)-2-phenyl acetonitrile |
| Boc-OSN | N-tert-butoxycarbonyloxy)succinimide; |
| Boc$_2$O | di-t-butyl carbonate |
| Bu$_4$NHSO$_4$ | butyl ammonium hydrogen sulphate |
| Cbz | carbobenzoxy (alternatively, benzyloxycarbonyl) |
| DCE | 1,2-dichloroethane |
| DCM | dichloromethane |
| DIPEA | diisopropylethylamine (or Hunig's base) |
| DMAC or DMAc | N,N-dimethylacetamide |
| DME | 1,2-dimethoxyethane |
| DMF | N,N-dimethylformamide |
| DMSO | dimethyl sulfoxide |
| Et | ethyl |
| EtOAc | ethyl acetate |
| GC | gas chromatography |
| HMDS | hexamethyldisilazide |
| HPLC | high-performance liquid chromatography |
| IPAc, iPrOAc | isopropyl acetate |
| IR | infrared |
| Me | methyl |
| MeCN | acetonitrile |
| MeOH | methanol |
| MTBE | methyl tert-butyl ether |
| 4-NMM | 4-methylmorpholine |
| NMP | N-methyl pyrrolidinone |
| NMR | nuclear magnetic resonance |
| Ns | Nitrobenzenesulfonyl |
| o-NsCl | 2-nitrobenzenesulfonyl chloride |
| pG | protective group |
| TBDPS | O-t-butyldiphenylsilyl |
| TBAOAc | tetra-n-butylammonium acetate |
| TBS | O-t-butyldimethylsilyl |
| t-Bu | tert-butyl |
| TEA | triethylamine |
| TFA | trifluoroacetic acid |
| THF | tetrahydrofuran |
| TIPS | O-triisopropylsilyl |
| TLC | thin layer chromatography |
| TMS | O-methylsilyl |
| TMSI | Trimethylsilyl iodide |
| TMSOTMS | Hexamethyldisiloxane |

The following examples serve only to illustrate the invention and its practice. The examples are not to be construed as limitations on the scope or spirit of the invention.

EXAMPLE 1

(2S,5R)-7-oxo-N-piperidin-4-yl-6-(sulfooxy)-1,6-diazabicyclo[3.2.1]octane-2-carboxamide

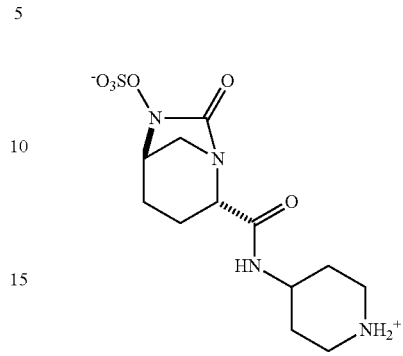

Step A: Preparation of (1S,4S)-5-((2-nitrophenyl)sulfonyl)-2-oxa-5-azabicyclo[2.2.2]octan-3-one (2)

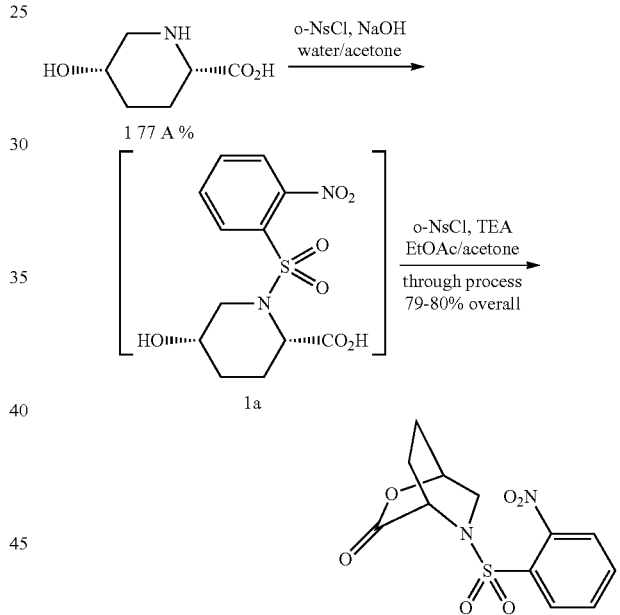

To a reactor (R-1) equipped with an additional funnel, nitrogen inlet and agitator was charged (2S,5S)-5-hydroxypiperidine-2-carboxylic acid (77.3 wt %) (50.0 g, 344 mmol), and water (150 mL). Agitation was begun, the pH adjusted to 10-11 by addition of 10 N NaOH (~46.5 mL) and the reactor charged with acetone (50.0 mL).

In a separate reactor (R-2) equipped with an agitator and nitrogen inlet was charged 2-nitrobenzene-1-sulfonyl chloride (97%) (106.0 g, 478 mmol) and acetone (80 mL). The contents of R-2 were transferred to R-1 at 23-30° C. while the pH of the solution was maintained at 10-11 by simultaneously addition of 10 N NaOH. After 15 to 30 min, the pH was adjusted to about 6 by addition of 12 N HCl. The solution was charged with EtOAc (500 mL) and the pH adjusted to 3.0 by addition of 12 N HCl. The layers were separated and the aqueous back-extracted with EtOAc (150 mL×2).

To a separate reactor (R-3) was charged product 1a in the combined organic layers, 2-nitrobenzene-1-sulfonyl chloride (73.0 g, 329 mmol), and triethylamine (130 mL). The batch in R-3 was agitated at 20-28° C. for 30 min. The solution was charged with water (100 mL), the layers separated, and the aqueous back extracted with EtOAc (150 mL×2). The combined EtOAc layer was washed with 10% NaHCO$_3$ (100 mL) and brine (100 mL). The organic phase was concentrated to 150 mL upon which a crystalline slurry was formed. The concentrated solution was agitated at 13-18° C. for 2-3 hours followed by filtration of crystalline solids. The resulting wet cake was washed with EtOAc (60 mL) and then dried under vacuum oven at 25-30° C. to afford 2 (65.6 g, 79% yield), m.p. 126.0-126.7° C. $^1$H NMR (CDCl$_3$, 400 MHz) δ: 8.02 (m, 1 H), 7.80-7.71 (m, 2 H), 7.66 (m, 1 H), 4.88 (m, 1 H), 4.55 (dd, J=3.8, 2.7 Hz, 1 H), 3.78 (dt, J=11.2, 3.0 Hz, 1 H), 3.66 (dd, J=11.2, 1.1 Hz, 1 H), 2.44 (m, 1 H), 2.11 (m, 2 H), 1.91 (m, 1 H); $^{13}$C NMR (CDCl$_3$, 100 MHz) δ: 168.4, 148.3, 134.4, 132.1, 131.0, 130.7, 124.2, 73.5, 51.4, 48.0, 25.1, 23.2

Step B: Preparation of tert-butyl 4-((2S,5S)-1-((2-nitrophenyl)sulfonyl)-5-(((2-nitrophenyl)sulfonyl)oxy)piperidine-2-carboxamido)piperidine-1-carboxylate (3)

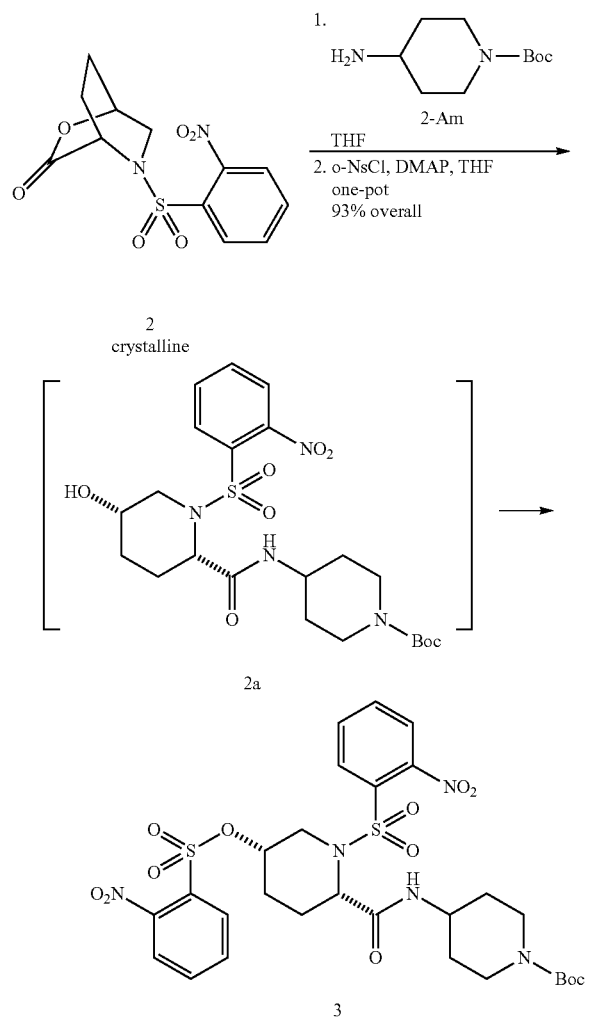

To a reactor (R-1) was charged lactone 2 (65.5 g, 210 mmol), THF (131 mL) and tert-butyl 4-aminopiperidine-1-carboxylate (44.5 g, 222 mmol). The stirred solution was heated to reflux (typical temperature 72° C.) for ~18 hr. The reaction was cooled to 25-35° C. and then charged with THF (325 mL) and 4-dimethylaminopyridine (40.1 g, 328 mmol) followed by agitation for 30 minutes.

To a separate reactor (R-2) was charged 2-nitrobenzene-1-sulfonyl chloride (60.9 g, 275 mmol) and THF (200 mL). The contents of R-2 were added to R-1 over the course of 45 to 75 minutes maintaining batch temperature of 20 to 30° C. The batch in R-1 was agitated for 2 to 4 hours at a temperature of 20 to 30° C.

To a separate reactor (R-3) was charged water (600 mL) and methanol (600 mL). The contents of R-3 were charged to the main batch over the course of 45 to 75 minutes with agitation while maintaining temperature of 20 to 30° C. The batch was cooled to 5 to −5° C. and then agitated at 5 to −5° C. for at least 4 hours. The solids were filtered and then washed twice with methanol (130 mL×2). The wet cake was dried in a vacuum oven at 40 to 50° C. to afford 3 (144.0 g, 98% yield), m.p. 131.8-133.1° C. $^1$H NMR (CDCl$_3$, 400 MHz) δ: 8.14 (m, 2H), 7.83-7.74 (m, 6H), 6.50 (d, J=7.9 Hz, 1 H), 4.69 (m, 1 H), 4.43 (s, 1H), 4.11 (dd, J=13.7, 4.9 Hz, 1H), 3.95 (m, 2H), 3.83 (m, 1H), 3.47 (s, 1H), 3.10 (dd, J=13.7, 11.0 Hz, 1H), 2.81 (m, 2H), 2.51 (m, 1H), 2.12 (m, 1H), 1.85-1.72 (m, 4H), 1.45 (s, 9H), 1.26 (m, 1H); $^{13}$C NMR (CDCl$_3$, 100 MHz) δ: 166.9, 154.6, 148.2, 147.6, 135.2, 134.8, 132.6, 132.5, 131.9, 131.6, 131.4, 129.7, 124.9, 124.7, 79.8, 76.5, 55.0, 47.1, 46.0, 31.8, 31.5, 28.4, 27.3, 24.4.

Preparation of N-4-nitrobenzene sulfonyl-O-benzylhydroxylamine

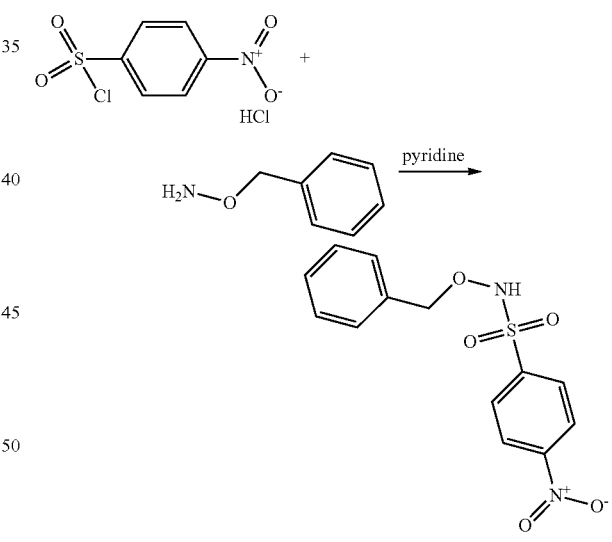

To a reactor (R-1) was charged O-benzylhydroxylamine hydrochloride (61.0 g, 382 mmol) and pyridine (400 mL). The solution cooled to 5 to −5° C.

To a separate reactor (R-2) was charged 4-nitrobenzenesulfonyl chloride (89.0 g, 402 mmol) and pyridine (200 mL). The contents of R-2 were transferred to R-1 at a rate to maintain temperature range of −5 to −5° C. The batch in R-1 was agitated at 5 to −5° C. for 15 to 45 minutes then warmed to 20 to 30° C. for 45 to 75 minutes. Water (250 mL) was then added at a rate to maintain 20 to 30° C. and agitated 5 to 15 minutes. The solids were filtered and the wet cake was washed with water (100 mL×3). The wet cake was dried in vacuum oven at 50° C. to afford N-4-nitrobenzenesulfonyl-O-benzylhydroxylamine (113.3 g, 96% yield), m.p. 128.4-130.0° C. $^1$H NMR (CDCl$_3$, 400 MHz) δ: 8.36 (d, J=8.9 Hz, 2 H), 8.11 (d, J=8.9 Hz, 2 H), 7.36 (m, 5H), 7.11 (s, 1H), 5.02 (s, 2H); $^{13}$C NMR (CDCl$_3$, 100 MHz) δ: 151.0, 142.5, 134.9, 130.2, 129.7, 129.3, 128.9, 124.5, 80.2.

Step C. Preparation of tert-butyl 4-((2S,5R)-5-((benzyloxy)amino)piperidine-2-carboxamido)piperidine-1-carboxylate (4)

40-50° C. to 165 mL, then cooled to 35-40° C. The batch was charged with seed (50 mg) and agitated for 1 h at 35-40° C. The batch was charged with heptanes (110 mL) at 35-40° C. over 1 h, then slowly cooled to 15-20° C. over 1 h. The batch was agitated for 3 h and the solids filtered. The wet cake was washed with toluene/heptanes (137.5 mL) then dried in vacuum oven at 30° C. for 3-8 h to affored 4. (47.3 g, 70% overall yield from 3), m.p. 117.5-118.0° C. $^1$H NMR (CDCl$_3$, 500 MHz) δ: 7.37-7.29 (m, 5 H), 6.64 (d, J=8.2 Hz, 1 H), 5.36 (brs, 1 H), 4.67 (s, 2 H), 4.00 (m, 2 H), 3.90 (m, 1 H), 3.28 (ddd, J=11.8, 4.0, 1.7 Hz, 1 H), 3.12 (dd, J=10.2,

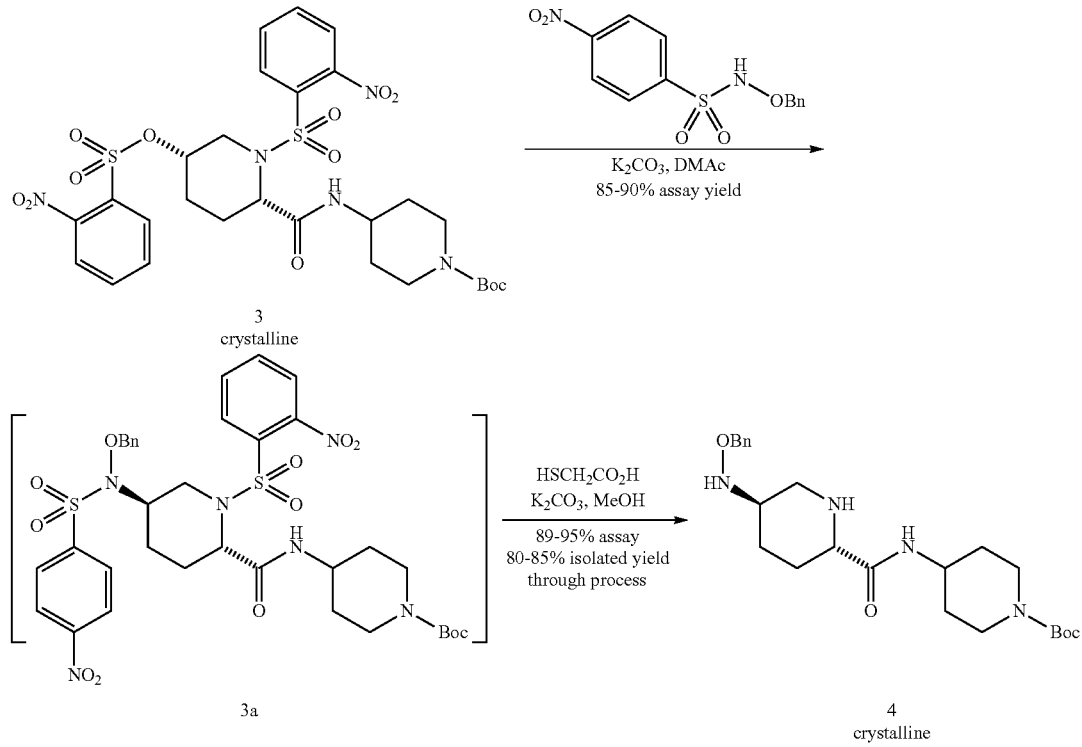

To a reactor (R-1) was charged tert-butyl 4-((2R,5R)-1-((2-nitrophenyl)sulfonyl)-5-(((2-nitrophenyl)sulfonyl)oxy) piperidine-2-carboxamido)piperidine-1-carboxylate (3) (110 g, 158 mmol), N-4-nitrobenzene sulfonyl-O-benzylhydroxylamine (58 g, 188 mmol), potassium carbonate (25.9 g, 187 mmol) and dimethylacetamide (440 mL). The stirred solution was heated to 60 to 70° C. for 24-32 hours. The batch was cooled to 20 to 30° C. and charged with toluene (660 mL). The batch was extracted with 1 N sodium hydroxide (3×220 mL) then washed with water (220 mL).

The toluene solution was azotropically distilled at ~50° C. to about ⅓ volume. The solution was solvent-switched to MeOH at 45-55° C., adjusted to 237 mL.

The batch was cooled to 20-25° C., charged with thioglycolic acid (57.9 g, 629 mmol) at 10° C., and then charged with K$_2$CO$_3$ anhydrous (172.0 g, 1225 mmol). The batch was agitated at 10-15° C. for 0.5 h, warmed to 20-25° C., agitated at 20-25° C. for 10-15 h, and heated at 48-53° C. for 3-6 h.

The batch was charged with 10 wt % sodium chloride (1.10 L) and toluene (880 mL) at about 40° C. The layers were separated and the aq. layer back-extracted with toluene (3×440 mL). The combined organic layer was washed with 10% NaHCO$_3$ (2×220 mL). The batch was concentrated at 3.2 Hz, 1 H), 2.95 (m, 1 H), 2.86 (m, 2 H), 2.46 (dd, J=11.8, 9.5 Hz, 1 H), 2.10 (m, 1 H), 1.93-1.83 (m, 3 H), 1.58 (brs, 1 H), 1.45 (s, 9 H), 1.41 (m, 1 H), 1.35-1.23 (m, 3 H); $^{13}$C NMR (CDCl$_3$, 125 MHz) δ: 172.8, 154.7, 137.7, 128.4 (4C), 127.9, 79.6, 76.9, 59.8, 57.0, 49.2, 46.1, 42.8 (br, 2C), 32.0 (2C), 28.4 (3C), 28.3, 27.2.

Step D: Preparation of tert-butyl 4-((1R,2S,5R)-6-(benzyloxy)-7-oxo-1,6-diazabicyclo[3.2.1]octane-2-carboxamido)piperidine-1-carboxylate (5)

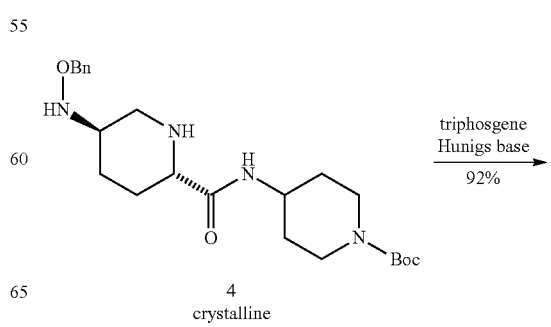

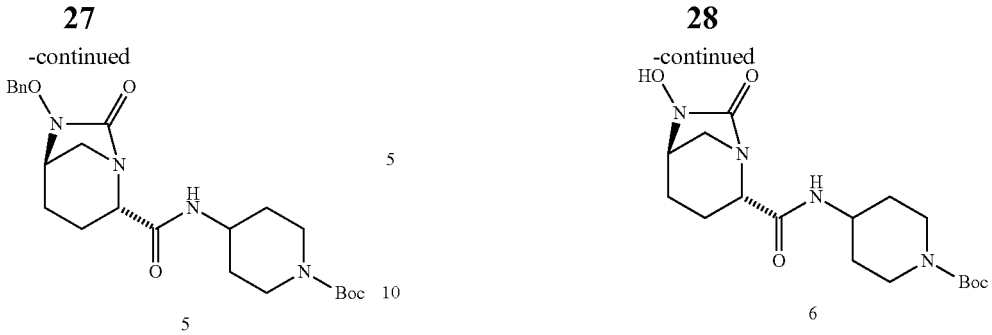

To a reactor (R-1) was charged tert-butyl 4-((2S,5R)-5-((benzyloxy)amino)piperidine-2-carboxamido)piperidine-1-carboxylate (4) (46.3 g, 107 mmol), dichloromethane (463 mL), and Hunig's base (58.0 mL). The batch was cooled to −18° C. and then charged with triphosgene in four portions (25.1 g total; 85 mmol) at <−8° C. The batch was agitated at −5 to 0° C. for 0.5 h then charged with 11.4 wt % aqueous $H_3PO_4$ at −5 to 0° C. (347 g, 3541 mmol). The batch was agitated at 20-25° C. for 15-20 h then phase cut. The aqueous layer was back-extracted with dichloromethane (138 mL). The combined organic layer was washed with 10% $NaHCO_3$ (115 mL), then water (115 mL). The organic solution was concentrated at atmospheric pressure to ~80 mL, then charged with MTBE (347 mL) at 35-45° C. over 0.5 h, then concentrated at 35-45° C. to 231 mL two times to form a slurry.

The slurry was charged with heptanes (139 mL) at 35-45° C. over 2 h, then slowly cooled to 15-20° C. over 1 h. The batch was agitated at 15-20° C. for 6-8 h. Solids were filtered and the wet cake washed with MTBE/heptanes (1.4:1, 185 mL) then dried under vacuum at 25-30° C. for 5-10 hours to afford 5 (43.7 g, 92% yield), m.p. 161.3-161.8° C. $^1H$ NMR ($CDCl_3$, 500 MHz) δ: 7.45-7.32 (m, 5 H), 6.55 (d, J=8.2 Hz, 1 H), 5.05 (d, J=11.6 Hz, 1 H), 4.90 (d, J=11.6 Hz, 1 H), 4.02 (m, 2 H), 3.90 (m, 2 H), 3.30 (m, 1 H), 2.99 (dt, J=11.7, 1.1 Hz, 1 H), 2.86 (m, 2 H), 2.64 (d, J=11.7 Hz, 1 H), 2.37 (dd, J=14.6, 6.9 Hz, 1 H), 2.04-1.82 (m, 4 H), 1.58 (m, 1 H), 1.45 (s, 9 H), 1.30 (m, 2 H); $^{13}C$ NMR ($CDCl_3$, 125 MHz) δ: 168.3, 167.5, 154.7, 135.6, 129.2 (2C), 128.8, 128.6 (2C), 79.7, 78.3, 60.4, 57.8, 47.5, 46.8, 42.5 (br, 2C), 32.0, 31.7, 28.4 (3C), 20.8, 17.2.

Step E: Preparation of tert-butyl 4-((2S,5R)-6-hydroxy-7-oxo-1,6-diazabicyclo[3.2.1]octane-2-carboxamido)piperidine-1-carboxylate tert-butyl 4-((2S,5R)-6-hydroxy-7-oxo-1,6-diazabicyclo[3.2.1]octane-2-carboxamido)piperidine-1-carboxylate (9.2 g, 20.1 mmol) was charged to a glass bottle, and the solids were dissolved in THF (150 mL). The solution was then charged to a hydrogenation reactor along with $Pd/Al_2O_3$ (10 wt %, 1.5 g). The reaction was purged three times with hydrogen and then set to a hydrogen pressure of 50 psi. The reaction temperature was adjusted to 25° C. and the reaction was allowed to agitate for 22 hours. After the reaction was complete as determined by HPLC analysis, the solution was filtered through SOLKA-FLOC® (Interational Fiber Corporation, North Tonawanda, N.Y.) to remove the catalyst and the filter cake was washed with THF. The filtrate and washes were then solvent switched by vacuum distillation to iPrOAc to a final volume of 40 mL. The resulting iPrOAc slurry was aged at room temperature for 1 hour. The solids were then filtered and washed with iPrOAc (20 mL) and dried under vacuum and $N_2$ at 40° C. to afford the title product (6.62 g, 17.97 mmol, 90% isolated yield). Spectral data matched the reference compound.

Preparation of (2S,5R)-7-oxo-N-piperidin-4-yl-6-(sulfooxy)-1,6-diazabicyclo[3.2.1]octane-2-carboxamide

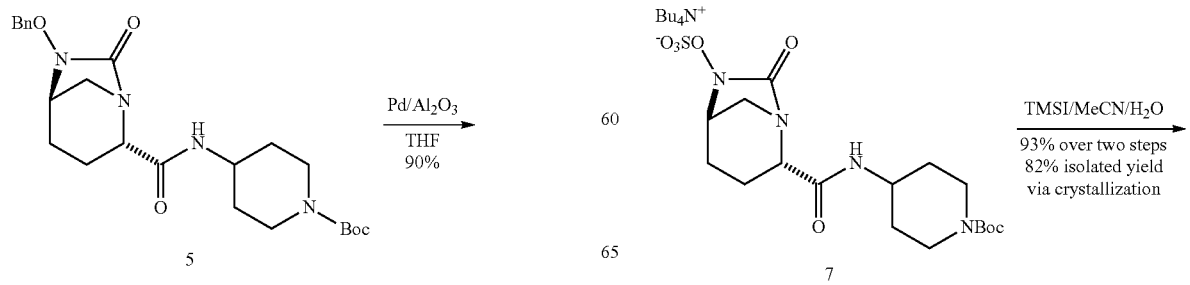

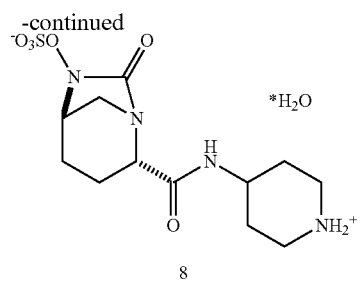

8 tert-butyl 4-((2S,5R)-6-hydroxy-7-oxo-1,6-diazabicyclo[3.2.1]octane-2-carboxamido)piperidine-1-carboxylate (20 g, 54.3 mmol), THF (200 mL), 2-picoline (10.9 mL, 309 mmol) and pyridine-SO₃ complex (30.2 g, 190 mmol) were charged to a flask under nitrogen. The heterogeneous mixture was allowed to stir overnight (~15 h). The reaction mixture was cooled to −10° C. then DCM (200 mL) was added. 0.5 M K₂HPO₄ (168 mL, 84 mmol) was added over 10 minutes. Bu₄NHSO₄ (19.4 g, 57 mmol) was then added over 10 minutes. The biphasic mixture was stirred for 30 minutes, phase cut and the water layer was back extracted with 40 ml of DCM. The combined DCM solution was washed with water (120 ml), phase cut and the organic solution was solvent-switched to MeCN (320 ml) by vacuum distillation with 3 bed volumes of MeCN (total 1.0 L) and used as is in the next step. The solution of Bu₄N⁺⁻OSO₃ salt 7 in MeCN solution was used with an assumed yield of 100% (37.5 g, 54.3 mmol). The reaction mixture was cooled in an ice bath, and TMSI (10.26 ml, 70.7 mmol) was added via addition funnel over 30 minutes between 0° C. and 5° C. The resulting mixture was agitated for 1-2 h and then quenched with H₂O:MeCN (1:1, 6 ml) to afford a slurry. The slurry was warmed to room temperature and agitated for 12 h and after this time the pH of the supernatant was about 3.0. Tetrabutylammonium acetate (13.6 ml, 13.59 mmol) was slowly added over 30 min. The slurry was agitated for 1 h and pH of the supernatant was about 4.0. Solids were collected by filtration. The solid was washed with 60 mL of aqueous MeCN to afford 19.5 g of the crude product 8 in a 93% isolated yield from compound 6.

At this stage, all byproducts (including hydrolyzation products of TMS-carbonate) and impurities were soluble in the organic phase.

The product was dissolved back into 140 ml of MeCN:H₂O (1:2) at room temperature. 1-Butanol (390 ml) as antisolvent was slowly added into the solution to afford a slurry. The slurry was agitated overnight. The white crystalline solid was filtered and washed with 3:1 IPA:water (40 ml) and dried under vacuum and nitrogen at room temperature to afford the title product in the form of a crystalline hydrate. (Yield=16.3 g, 82%). Spectral data matched reference compound.

Preparation of (2S,5R)-7-oxo-2-(piperidin-1-ium-4-ylcarbamoyl)-1,6-diazabicyclo[3.2.1]octan-6-yl sulfate (1)

tert-Butyl 4-(\{[(2S,5R)-6-hydroxy-7-oxo-1,6-diazabicyclo[3.2.1]oct-2-yl]carbonyl\}amino)piperidine-1-carboxylate 16 (0.54 g, 1.5 mmol), THF (5.4 mL), 2-picoline (0.29 mL, 2.9 mmol) and pyridine-SO₃ complex (0.70 g, 4.4 mmol) were charged to a vial under nitrogen. The heterogeneous mixture was allowed to stir overnight (~15 hr). The reaction mixture was cooled to −10° C. then dichloromethane (5.4 mL) was added. 0.5 M K₂HPO₄ (4.5 mL, 2.3 mmol) was added over 10 minutes. Bu₄NHSO₄ (0.53 g, 1.54 mmol) was then added over 10 min. The biphasic mixture was stirred for 30 min, phase cut and the water layer was back extracted with 1 ml of DCM. The combined DCM solution was washed with water (2.0 mL), phase cut and the organic solution was solvent-switched to MeCN (3.2 mL) by vacuum distillation with 3 bed volumes of MeCN. The product was used as is in the next step (water content less than 1000 ppm).

The solution of Bu₄N⁺SO₄⁻ salt 8 in MeCN solution was used with an assumed yield of 100% (1.0 g, 1.47 mmol). The reaction mixture was cooled in an ice bath, and N,O-bis(trimethylsilyl)trifluoroacetamide (BSTFA) (0.41 g, 1.59 mmol) was added into the reaction and was allowed to stir for 10 min. TMSI (0.06 g, 0.27 mmol) was added between 0° C. and 5° C. The resulting mixture was allowed to agitate for 2 hr and then quenched with H₂O (0.07 g, 4.1 mmol) and acetic acid (0.08 g, 1.5 mmol) to afford a slurry. The slurry was warmed to room temperature and agitated for 12 hr. Filter to collect the solid. The solid was washed with MeCN/water (94:6, 1 mL×4) to afford the crystalline product 1 (0.38 g) in a 75% yield.

If N, O-bis(trimethylsilyl)acetamide (BSA) (0.32 g, 1.59 mmol) was applied, the reaction needed 24 hr to achieve full conversion.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing a compound of Formula III:

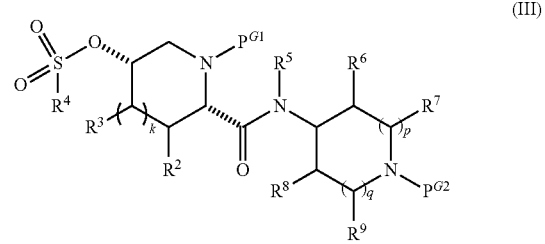

(III)

which comprises:

(A) contacting a lactone of Formula II:

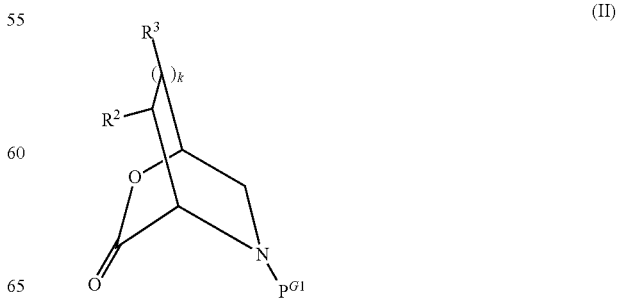

(II)

with an azacycloalkylamine of formula II-Am:

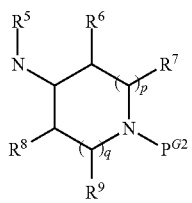

(II-Am)

followed by contact with a sulfonyl halide of formula II-Su:

R⁴—SO₂W  (II-Su)

in the presence of tertiary amine base to obtain a compound of Formula III wherein:
$P^{G1}$ is a first amine protecting group which forms with the amino nitrogen to which it is attached a carbamate, a benzylamine, or a sulfonamide;
$P^{G2}$ is a second amine protecting group selected from (i) carbamates and (ii) benzylamines;
k is an integer equal to 0, 1, or 2;
$R^2$ and $R^3$ are defined as follows:
  (a) $R^2$ is H, $C_{1-6}$ alkyl, —O—$C_{1-6}$ alkyl, —O—Si(—$C_{1-6}$ alkyl)₃, or —O—Si(—$C_{1-6}$ alkyl)(-phenyl)₂, and each $R^3$ is H or $C_{1-6}$ alkyl; or
  (b) alternatively and with the proviso that k is 1 or 2, $R^2$ and the $R^3$ adjacent to $R^2$ together with the carbon atoms to which each is attached form $C_{5-7}$ cycloalkyl which is optionally substituted with from 1 to 3 substituents each of which is independently $C_{1-6}$ alkyl, —O—$C_{1-6}$ alkyl, —O—Si(—$C_{1-6}$ alkyl)₃, or —O—Si(—$C_{1-6}$ alkyl) (-phenyl)₂; and any other $R^3$ is H or $C_{1-6}$ alkyl;
$R^4$ is
  (1) phenyl optionally substituted with from 1 to 3 substituents each of which is independently $C_{1-4}$ alkyl, $C_{1-4}$ haloalkyl, —O—$C_{1-4}$ alkyl, —O—$C_{1-4}$ haloalkyl, Cl, Br, F, or NO₂;
  (2) $C_{1-4}$ alkyl; or
  (3) $C_{1-4}$ haloalkyl;
$R^5$ is H or $C_{1-3}$ alkyl;
$R^6$ and $R^8$ are independently H, $C_{1-3}$ alkyl, —O—$C_{1-3}$ alkyl, or N(—$C_{1-3}$ alkyl)₂;
each $R^7$ and $R^9$ is independently H or $C_{1-6}$ alkyl
W is halogen;
p is 0, 1, or 2;
q is 0, 1, or 2; and
p+q=2.

2. The process according to claim 1, which further comprises:
(A) contacting a compound of Formula I:

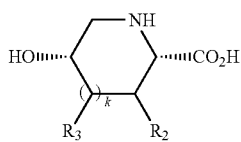

(I)

with a $P^{G1}$-producing agent in the presence of an organic or inorganic base to obtain Compound II.

3. The process according to claim 1, which further comprises:
(A) contacting a compound of Formula I:

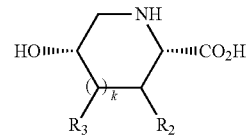

(I)

with a $P^{G1}$-producing agent in the presence of an aqueous base followed by addition of a tertiary base to obtain Compound II.

4. The process according to claim 1, which further comprises:
(C) treating Compound III with N-4-nitrobenzene sulfonyl-O-benzylhydroxylamine in the presence of a base, followed by treatment with a thiol to obtain compound of Formula IV, or a pharmaceutically acceptable salt thereof:

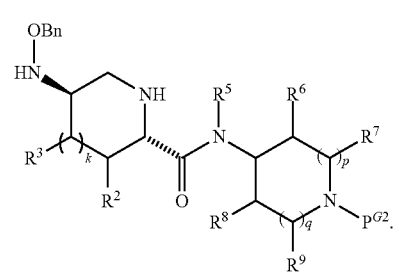

(IV)

5. The process according to claim 1, which further comprises:
(D) contacting Compound (IV) with phosgene, diphosgene, triphosgene, carbodiimidazole or haloformate in the presence of a amine base, and then quenching with aqueous medium to obtain a compound of Formula V:

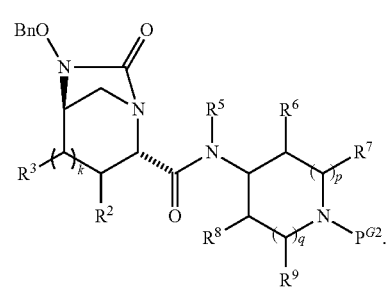

(V)

6. The process according to claim 1, which further comprises:
(D) contacting Compound (IV) with phosgene, diphosgene, or triphosgene in the presence of a tertiary amine, and then adding an aqueous solution of acid to obtain a compound of Formula V:

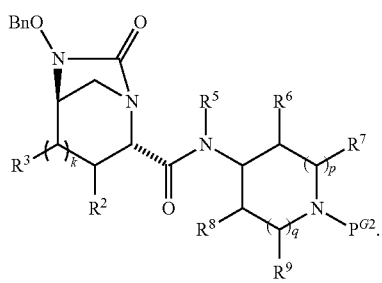

(V)

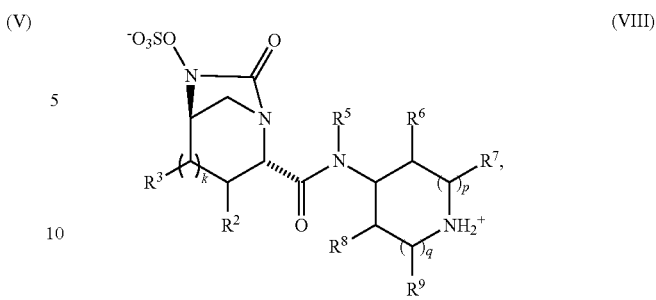

(VIII)

or a pharmaceutically acceptable salt thereof.

10. A process according to claim 1, wherein the compound of Formula III is Compound 3:

7. The process according to claim 5, which further comprises:

(E) contacting Compound V with a source of hydrogen in the presence of a hydrogenolysis catalyst and in the presence of a Boc-producing agent to obtain a compound of Formula VI:

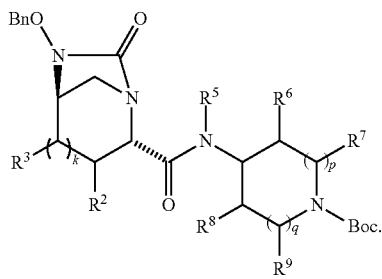

(VI)

(3)

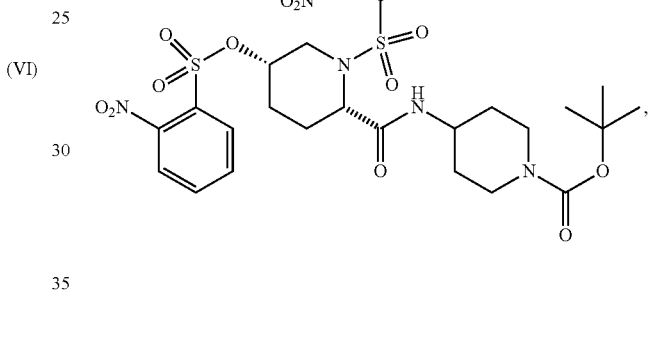

which comprises:

(B) contacting a lactone 2:

8. The process according to claim 7, which further comprises:

(F) contacting compound VI with a sulfating agent in the presence of an organic base to obtain a compound of Formula VII, or a pharmaceutically acceptable salt thereof:

(2)

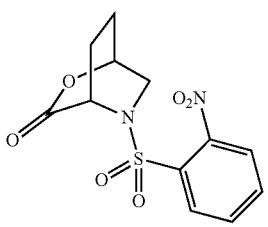

(VII)

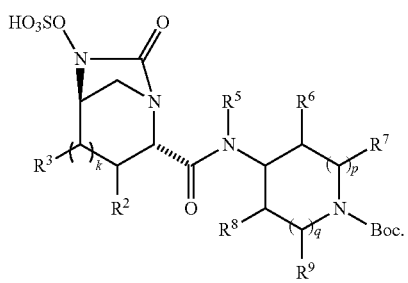

with an azacycloalkylamine 2-Am:

(2-Am)

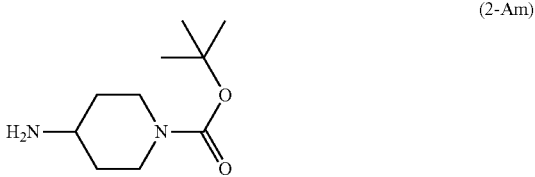

9. The process according to claim 8, which further comprises:

(G) treating compound VII with acid to obtain a compound of Formula VIII:

followed by contact with a sulfonyl halide 2-Su:

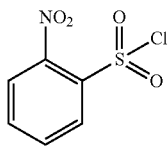
(2-Su)

in the presence of 4-dimethylaminopyridine.

11. The process according to claim 9, which further comprises:

(A) contacting a compound 1, or a pharmaceutically acceptable salt thereof:

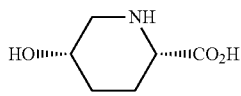
(1)

with 2-nitrobenzene-1-sulfonyl chloride in the presence of an organic or inorganic base to obtain compound 2.

12. The process according to claim 10, which further comprises:

(A) contacting a compound 1, or a pharmaceutically acceptable salt thereof:

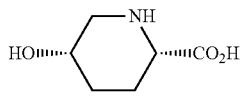
(1)

with 2-nitrobenzene-1-sulfonyl chloride in the presence of an aqueous base followed by addition of TEA, DIPEA or diethylisopropylamine to obtain compound 2.

13. The process according to claim 11, which further comprises:

(C) treating Compound 3 with N-4-nitrobenzenesulfonyl-O-benzylhydroxylamine in the presence of a base, followed by treatment with a thiol to obtain compound 4, or a pharmaceutically acceptable salt thereof:

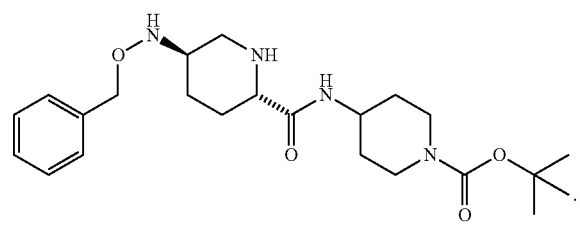
(4)

14. The process according to claim 13, which further comprises:

(D) contacting compound 4 with phosgene, diphosgene, triphosgene, carbodiimidazole or haloformate in the presence of an amine base, and then quenching with aqueous medium to obtain a compound 5:

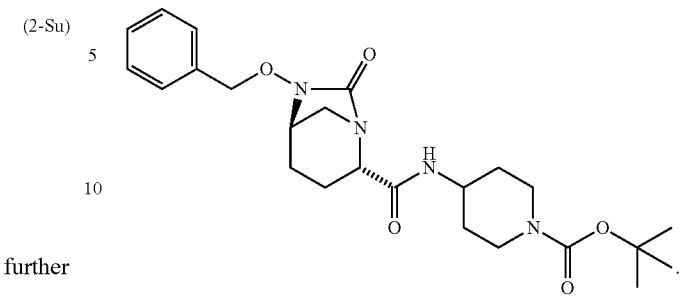
(5)

15. The process according to claim 13, which further comprises:

(D) contacting compound 4 with phosgene, diphosgene, or triphosgene in the presence of a tri-$C_{1-4}$ alkylamine, and then adding an aqueous solution of acid to obtain a compound 5:

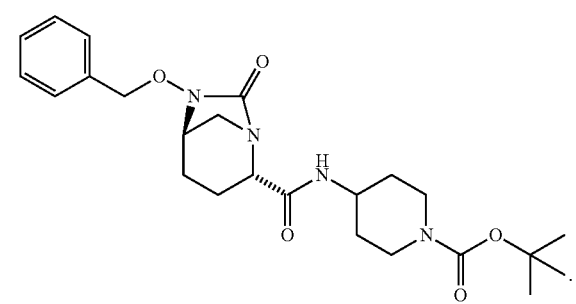
(5)

16. The process according to claim 14, which further comprises:

(E) contacting compound 5 with hydrogen in the presence of a Pd catalyst to obtain compound 6:

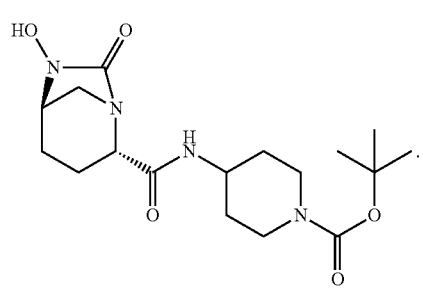
(6)

17. The process according to claim 16, which further comprises:

(F) contacting compound 6 with a sulfating agent selected from the group consisting of pyridine-$SO_3$ complex, chlorosulfonic acid and DMF-$SO_3$ complex in the presence of 2-picoline to obtain compound 7, or a pharmaceutically acceptable salt thereof:

(7)

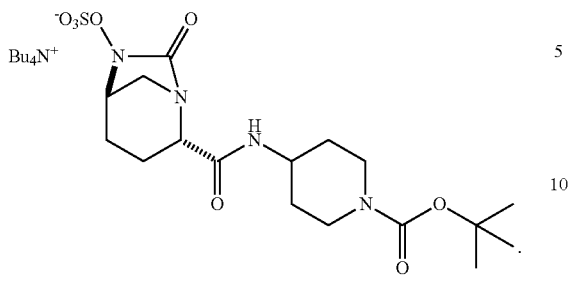

18. The process according to claim 16, which further comprises:

(F) contacting compound 6 with a sulfating agent selected from the group consisting of pyridine-SO$_3$ complex, chlorosulfonic acid and DMF-SO$_3$ complex in the presence of picoline to obtain compound 7, or a pharmaceutically acceptable salt thereof:

(7)

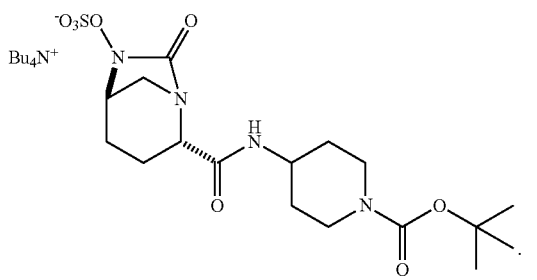

19. The process according to claim 17, which further comprises:

(G) treating Compound 7 with acid to obtain Compound 8:

(8)

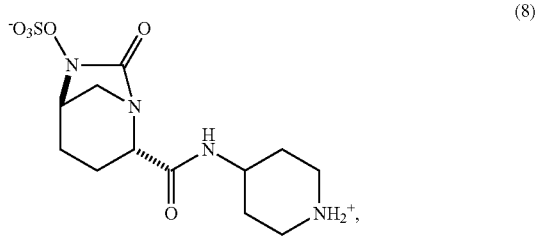

or a pharmaceutically acceptable salt thereof.

20. The process according to claim 19, wherein the acid is trimethylsilyl iodide (TMSI).

21. The process according to claim 20, wherein the TMSI is in the presence of N,O-Bis(trimethylsilyl)acetamide (BSA) or N,O-bis(trimethylsilyl)trifluoroacetamide (BSTFA).

22. The process of claim 19, wherein Compound 8 is directly crystallized as a monohydrate from the reaction mixture.

23. A compound selected from the group consisting of:

(III)

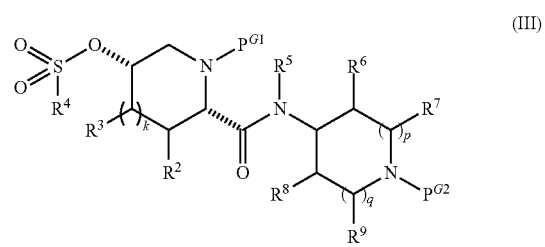

wherein:

$P^{G1}$ is a first amine protecting group which forms with the amino nitrogen to which it is attached a carbamate, a benzylamine, or a sulfonamide;

$P^{G2}$ is a second amine protecting group selected from the group consisting of (i) carbamates or (ii) benzylamines k is an integer equal to 0, 1, or 2;

$R^2$ and $R^3$ are defined as follows:

(a) $R^2$ is H, $C_{1-6}$ alkyl, —O—$C_{1-6}$ alkyl, —O—Si(—$C_{1-6}$ alkyl)$_3$, or —O—Si(—$C_{1-6}$ alkyl)(-phenyl)$_2$, and each $R^3$ is H or $C_{1-6}$ alkyl; or (b) alternatively and with the proviso that k is 1 or 2, $R^2$ and the $R^3$ adjacent to $R^2$ together with the carbon atoms to which each is attached form $C_{5-7}$ cycloalkyl which is optionally substituted with from 1 to 3 substituents each of which is independently $C_{1-6}$ alkyl, —O—$C_{1-6}$ alkyl, —O—Si(—$C_{1-6}$ alkyl)$_3$, or —O—Si(—$C_{1-6}$ alkyl) (-phenyl)$_2$; and any other $R^3$ is H or $C_{1-6}$ alkyl;

$R^4$ is:

(1) phenyl optionally substituted with from 1 to 3 substituents each of which is independently $C_{1-4}$ alkyl, $C_{1-4}$ haloalkyl, —O—$C_{1-4}$ alkyl, —O—$C_{1-4}$ haloalkyl, Cl, Br, F, or NO$_2$;

(2) $C_{1-4}$ alkyl; or (3) $C_{1-4}$ haloalkyl;

$R^5$ is H or $C_{1-3}$ alkyl;

$R^6$ and $R^8$ are independently H, $C_{1-3}$ alkyl, O—$C_{1-3}$ alkyl, or N(—$C_{1-3}$ alkyl)$_2$;

each $R^7$ and $R^9$ is independently H or $C_{1-6}$ alkyl;

W is halogen;

p is 0, 1, or 2;

q is 0, 1, or 2; and p+q=2.

24. A compound according to claim 23, which is selected from the group consisting of:
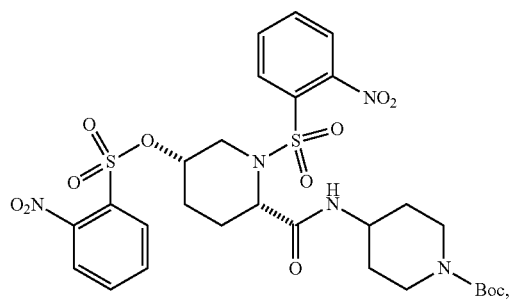
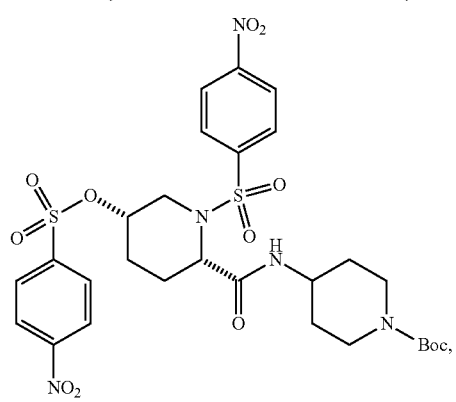
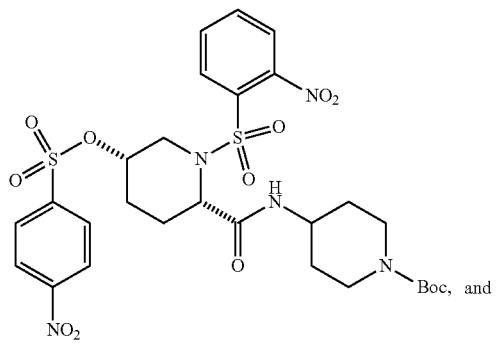
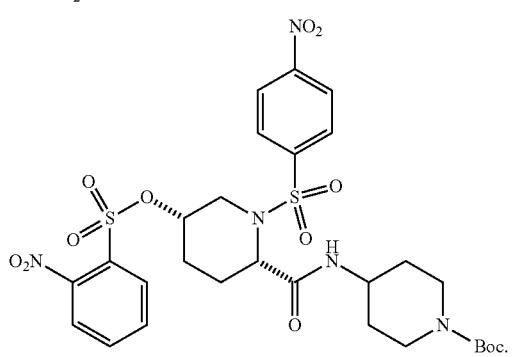
* * * * *

UNITED STATES PATENT AND TRADEMARK OFFICE
CERTIFICATE OF CORRECTION

PATENT NO. : 9,604,985 B2  
APPLICATION NO. : 14/897290  
DATED : March 28, 2017  
INVENTOR(S) : Steven P. Miller et al.

Page 1 of 1

It is certified that error appears in the above-identified patent and that said Letters Patent is hereby corrected as shown below:

In Item (54) replace "1-CARB" with --1-CARBOXYLATE--

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*